(12) United States Patent
Lukashev et al.

(10) Patent No.: US 8,399,514 B2
(45) Date of Patent: Mar. 19, 2013

(54) TREATMENT FOR MULTIPLE SCLEROSIS

(75) Inventors: Matvey E. Lukashev, Tewksbury, MA (US); Gilmore O'Neill, Medford, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 13/372,426

(22) Filed: Feb. 13, 2012

(65) Prior Publication Data

US 2012/0196931 A1 Aug. 2, 2012

Related U.S. Application Data

(63) Continuation of application No. 12/526,296, filed as application No. PCT/US2008/001602 on Feb. 7, 2008, now abandoned.

(60) Provisional application No. 60/888,921, filed on Feb. 8, 2007.

(51) Int. Cl.
*A61K 31/22* (2006.01)

(52) U.S. Cl. ..................................................... 514/549

(58) Field of Classification Search ........................ None
See application file for complete search history.

(56) References Cited

U.S. PATENT DOCUMENTS

| | | | |
|---|---|---|---|
| 4,515,974 A | 5/1985 | Zecher et al. |
| 4,746,668 A | 5/1988 | Sato et al. |
| 4,851,439 A | 7/1989 | Speiser et al. |
| 4,959,389 A | 9/1990 | Speiser et al. |
| 5,149,695 A | 9/1992 | Speiser et al. |
| 5,214,196 A | 5/1993 | Blank |
| 5,242,905 A | 9/1993 | Blank |
| 5,359,128 A | 10/1994 | Blank |
| 5,424,332 A | 6/1995 | Speiser et al. |
| 5,451,667 A | 9/1995 | Speiser et al. |
| 5,538,968 A | 7/1996 | Chiesi et al. |
| 5,548,059 A | 8/1996 | Bayley et al. |
| 5,972,363 A | 10/1999 | Clikeman et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 | 1/2003 | Joshi et al. |
| 6,812,248 B2 | 11/2004 | Zhang et al. |
| 6,858,750 B2 | 2/2005 | Joshi et al. |
| 7,056,950 B2 | 6/2006 | Rath |
| 7,157,423 B2 | 1/2007 | Joshi et al. |
| 7,279,331 B2 | 10/2007 | Black et al. |
| 7,320,999 B2 | 1/2008 | Joshi et al. |
| 7,364,900 B2 | 4/2008 | Black et al. |
| 7,417,045 B2 | 8/2008 | Anilkumar et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,638,119 B2 | 12/2009 | Johnson et al. |
| 7,790,916 B2 | 9/2010 | Joshi et al. |
| 7,803,840 B2 | 9/2010 | Joshi et al. |
| 7,871,977 B2 | 1/2011 | Rischer et al. |
| 7,906,659 B2 | 3/2011 | Joshi et al. |
| 7,915,310 B2 | 3/2011 | Joshi et al. |
| 8,067,467 B2 | 11/2011 | Joshi et al. |
| 2003/0176365 A1 | 9/2003 | Blass |
| 2004/0054001 A1 | 3/2004 | Joshi et al. |
| 2005/0245612 A1 | 11/2005 | Blass |
| 2007/0027076 A1 | 2/2007 | Joshi et al. |
| 2008/0089861 A1 | 4/2008 | Went et al. |
| 2008/0233185 A1 | 9/2008 | Joshi et al. |
| 2010/0130607 A1 | 5/2010 | Gold |
| 2011/0112196 A1 | 5/2011 | Lukashev |
| 2011/0124615 A1 | 5/2011 | Joshi et al. |
| 2011/0293711 A1 | 12/2011 | Joshi et al. |
| 2012/0165404 A1 | 6/2012 | Lukashev |

FOREIGN PATENT DOCUMENTS

| | | |
|---|---|---|
| CA | 2248955 A1 | 5/1997 |
| CN | 1125141 A | 6/1996 |
| DE | 25 30 372 A1 | 1/1977 |
| DE | 26 21 214 A1 | 11/1977 |
| DE | 28 40 498 B1 | 8/1979 |
| DE | 38 34 794 A1 | 4/1990 |
| DE | 197 21 099 A1 | 11/1998 |
| EP | 0 188 749 A2 | 7/1986 |
| EP | 0 312 697 A2 | 4/1989 |
| EP | 0 518 388 A2 | 12/1992 |
| EP | 0 793 966 A1 | 9/1997 |
| EP | 0 852 233 A1 | 7/1998 |
| GB | 2 291 422 A | 1/1996 |
| JP | 54-80439 A | 6/1979 |
| JP | 6-345644 A | 12/1994 |
| JP | 8-99906 A | 4/1996 |
| JP | 9-221428 A | 8/1997 |
| RU | 2 189 813 C1 | 9/2002 |
| WO | WO 89/01930 A1 | 3/1989 |
| WO | WO 94/28883 A1 | 12/1994 |
| WO | WO 95/25102 A1 | 9/1995 |
| WO | WO 96/01122 A1 | 1/1996 |
| WO | WO 96/08970 A1 | 3/1996 |
| WO | WO 97/09984 A1 | 3/1997 |
| WO | WO 97/13504 A1 | 4/1997 |

(Continued)

OTHER PUBLICATIONS

Thomson Innovation Patent Record, DWPI Accession No. 1979-58797B, English Abs. language Abstract of Japanese Patent Publication No. 54-80439 A, (1979).

(Continued)

*Primary Examiner* — John Ulm

(74) *Attorney, Agent, or Firm* — Sterne, Kessler, Goldstein & Fox P.L.L.C.

(57) ABSTRACT

Provided are certain methods of screening, identifying, and evaluating neuroprotective compounds useful for treatment of neurological diseases, such as, e.g., multiple sclerosis (MS). The compounds described upregulate the cellular cytoprotective pathway regulated by Nrf2. Also provided are certain methods of utilizing such compounds in therapy for neurological disease, particularly, for slowing or reducing demyelination, axonal loss, or neuronal and oligodendrocyte death.

20 Claims, 4 Drawing Sheets

FOREIGN PATENT DOCUMENTS

| WO | WO 97/44054 A2 | 11/1997 |
|---|---|---|
| WO | WO 97/48405 A1 | 12/1997 |
| WO | WO 98/04290 A2 | 2/1998 |
| WO | WO 98/27970 A2 | 7/1998 |
| WO | WO 99/21565 A1 | 11/1998 |
| WO | WO 01/59072 A1 | 8/2001 |
| WO | WO 02/02190 A2 | 1/2002 |
| WO | WO 02/38142 A2 | 5/2002 |
| WO | WO 02/064129 A2 | 8/2002 |
| WO | WO 03/020908 A2 | 3/2003 |
| WO | WO 03/032969 A2 | 4/2003 |
| WO | WO 2005/023241 A1 | 3/2005 |
| WO | WO 2005/027899 A1 | 3/2005 |
| WO | WO 2006/037342 A2 | 4/2006 |
| WO | WO 2006/050730 A1 | 5/2006 |
| WO | WO 2006/055871 A2 | 5/2006 |
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2007/005879 A2 | 1/2007 |
| WO | WO 2007/006307 A2 | 1/2007 |
| WO | WO 2007/042034 A1 | 4/2007 |
| WO | WO 2007/042035 A2 | 4/2007 |
| WO | WO 2008/096271 A2 | 8/2008 |
| WO | WO 2008/097596 A2 | 8/2008 |
| WO | WO 2011/100589 A1 | 8/2011 |

OTHER PUBLICATIONS

English language Abstract of German Patent Publication No. DE 38 34 794 A1, European Patent Office, Espacenet database—Worldwide (2001).

English language Abstract of Japanese Patent Publication No. JP 6-345644 A, European Patent Office, Espacenet database—Worldwide (2001).

English language Abstract of Japanese Patent Publication No. JP 8-99906 A, European Patent Office, Espacenet database—Worldwide (2001).

English language Abstract of Japanese Patent Publication No. JP 9-221428 A, European Patent Office, Espacenet database—Worldwide (2001).

English language Abstract of WIPO Patent Publication No. WO 97/48405 A1, European Patent Office, Espacenet database—Worldwide (2001).

English language Abstract of Russian Patent Publication No. RU 2 189 813 C1, European Patent Office, Espacenet database—Worldwide (2002).

English language Abstract of WIPO Patent Publication No. WO 2005/027899 A1, European Patent Office, Espacenet database—Worldwide (2005).

Altmeyer, P.J., et al., "Antipsoriatic effect of fumaric acid derivatives Results of a multicenter double-blind study in 100 patients," *Journal of the American Academy of Dermatology* 30(6):977-981, American Academy of Dermatology, Inc., United States (1994).

Andersson, M., et al., "Cytokine profile in interferon-β treated multiple sclerosis patients: reduction of interleukin-10 mRNA expressing cells in peripheral blood," *Eur. J. Neurol.* 4:567-571, Rapid Science Publishers, England (1997).

Bacharach-Buhles, M., et al., "Fumaric Acid Esters (FAEs) Suppress CD 15- and ODP 4-positive Cells in Psoriasis," *Acta. Derm. Venereol. Suppl.* (Stockh) 186:79-82, Scandinavian University Press, Norway (1994).

Balashov, K.E., et al., "Defective regulation of IFNγ and IL-12 by endogenous IL-10 in progressive MS," *Neurology* 55:192-198, AAN Enterprises, Inc., United States (2000).

Becanovic, K., et al., "Paradoxical effects of arthritis-regulating chromosome 4 regions on myelin oligodendrocyte glycoprotein-induced encephalomyelitis in congenic rats," *Eur. J. Immunol.* 33:1907-1916, Wiley-VCH Verlag GmbH & Co. KGaA, Germany (2003).

Bettelli, E. and Nicholson, L.B., "The Role of Cytokines in Experimental Autoimmune Encephalomyelitis," *Arch. Immun. Ther. Exp.* 48:389-398, Warszawa, Panstwowy Zaklad Wydawn Lekarskich, Switzerland (2000).

Brown, T.R. and Kraft, G.H., "Multiple Sclerosis: A Paradigm Shift," *Phys. Med Rehabil. Clin. N. Am.* 16:xvii-xx, Elsevier Inc., United States (2005)

Cannella, B., et al., "IL-10 Fails to Abrogate Experimental Autoimmune Encephalomyelitis," *J. Neuroscience Research* 45:735-746, Wiley-Liss, Inc., United States (1996).

Correale, J., et al., "Sulfasalazine aggravates experimental autoimmune encephalomyelitis and causes an increase in the number of autoreactive T cells," *J. Neuroimmunol.* 34:109-120, Elsevier Science Publishers B.V., Netherlands (1991).

Dahlman, I., et al., "Quantitative trait loci disposing for both experimental arthritis and encephalomyelitis in the DA rat; impact on severity of myelin oligodendrocyte glycoprotein-induced experimental autoimmune encephalomyelitis and antibody isotype pattern," *Eur. J. Immunol.* 28:2188-2196, Wiley-VCH Verlag GmbH, Germany (1998).

Dal Canto, R.A., et al., "Local Delivery of TNF by Retrovirus-Transduced T Lymphocytes Exacerbates Experimental Autoimmune Encephalomyelitis," *Clinical Immunol.* 90(1):10-14, Academic Press, United States (1999).

De Graaf, K.L., et al., "MHC Class II Isotype- and Allele-Specific Attenuation of Experimental Autoimmune Encephalomyelitis," *J. Immunol.* 173:2792-2802, The American Association of Immunologists, Inc., United States (2004).

De Haan, P., "The Risk of Sensibilization and Contact Uritcaria upon Topical Application of Fumaric Acid Derivatives," *Dermatology* 188:126-130, Karger AG, Switzerland (1994).

De Jong, R., et al., "Selective stimulation of T helper 2 cytokine responses by the anti-psoriasis agent monomethylfumarate," *Eur. J. Immunol.* 26:2067-2074, Verlag Chemie GmbH, Germany (1996).

Del Prete, G., "The Concept of Type-1 and Type-2 Helper T Cells and Their Cyotkines in Humans," *Intern. Rev. Immunol.* 16:427-455, OPA (Overseas Publishers Association) Amsterdam B.V., England (1998).

Dethlefsen, L.A., "Toxic Effects of Acute Glutathione Depletion by Buthionine Sulfoximine and Dimethylfumarate on Murine Mammary Carcinoma Cells," *Radiation Res.* 114:215-224, Academic Press, Inc., United States (1988).

Di Marco, R., et al., "Curative effects of recombinant human Interleukin-6 in DA rats with protracted relapsing experimental allergic encephalomyelitis," *J. Neuroimmunol.* 116:168-177, Elsevier Science B.V., Netherlands (2001).

Di Rosa, F., et al., "Lack of Th2 cytokine increase during spontaneous remission of experimental allergic encephalomyelitis," *Eur. J. Immunol.* 28:3893-3903, Wiley-VCH Verlag GmbH, Germany (1998).

Djerbi, M., et al., "Expression of the Long Form of Human FLIP by Retroviral Gene Transfer of Hemopoietic Stem Cells Exacerbates Experimental Autoimmune Encephalomyelitis," *J. Immunol.* 170:2064-2073, The American Association of Immunologists, Inc., United States (2003).

Dücker, P. and Pfeiff, B., "Zwei Fälle von Nebenwirkungen einer Fumarsäureester—Lokaltharapie," *H+G Zeitschrift für Hautkrankheiten* 65:734-736, Grosse Verlag Berlin, Germany (1990) (Abstract Only in English).

Ferber, I.A., et al., "Mice with a Disrupted IFN-γ Gene Are Susceptible to the Induction of Experimental Autoimmune Encephalomyelitis (EAE)," *J. Immunol.* 156:5-7, The American Association of Immunologists, United States (1996).

Ferrante, P., et al., "Cytokine Production and Surface Marker Expression in Acute and Stable Multiple Sclerosis: Altered IL-12 Production and Augmented Signaling.Lymphocytic Activation Molecule (SLAM)-Expressing Lymphocytes in Acute Multiple Sclerosis," *J. Immunol.* 160:1514-1521, The American Association of Immunologists, United States (1998).

Fliegner, L. and Spiegel, P., "Osteomalazie als offenbar seltene Nebenwirkung der oralen Fumarsäuretherapie," *Hautarzt* 43:554-560, Springer-Verlag, Germany (1992) (Abstract Only in English).

Furlan, R., et al., "Interferon-β treatment in multiple sclerosis patients decreases the number of circulating T cells producing interferon-y and interleukin-4," *J. Neuroimmunol. 111*:86-92, Elsevier Science B.V., Netherlands (2000).

Galli, G., et al., "Macrophage-derived chemokine production by activated human T cells in vitro and in vivo: preferential association with the production of type 2 cytokines," *Eur. J. Immunol. 30*:204-210, Wiley-VCH Verlag GmbH, Germany (2000).

Gasser, M., et al., "Host Vs Graft and Graft Vs Host Reactions After Allogeneic Heterotopic Small Bowel Transplantation in the Rat," *Transplant. Proc. 24*(3):1128-1129, Appleton & Lange, United States (1992).

Genain, C.P., et al., "Late Complications of Immune Deviation Therapy in a Nonhuman Primate," *Science 274*:2054-2057, American Association for the Advancement of Science, United States (1996).

Ghoreschi, K. and Röcken, M., "Immune Deviation Strategies in the Therapy of Psoriasis," *Current Drug Targets—Inflammation & Allergy 3*:193-198, Bentham Science Publishers Ltd., Netherlands (2004).

Ghoreschi, K., et al., "Fumarates induce a DC2 phenotype in dendritic cells that establishes protective Th2 responses," *Arch. Dermatol. Forschung 296*:420, Springer Verlag, Germany (2005) (Abstract Only).

Ghoreschi, K., et al., "Fumaric acid ester an antipsoriatic drug abolishes the capacity of T cells to induce Th1-mediated autoimmune disease," *Arch. Dermatol. Res. 294*:28, Springer Verlag, Germany (2002) (Abstract Only).

Gielen, A.W., et al., "Expression of T cell immunoglobulin- and mucin-domain-containing molecules-1 and -3 (TIM-1 and -3) in the rat nervous and immune systems," *J. Neuroimmunol. 164*:93-104, Elsevier B.V., Netherlands (2005).

Gijbels, K., et al., "Administration of Neutralizing Antibodies to Interleukin-6 (IL-6) Reduces Experimental Autoimmune Encephalomyelitis and is Associated with Elevated Levels of IL-6 Bioactivity in Central Nervous System and Circulation," *Mol. Med 1*(7):795-805, Molecular Medicine, United States (1995).

Giovannoni, G. and Miller, D.H., "Multiple sclerosis and its treatment," *J. R. Coll. Physicians Lond 33*(4):315-322, Royal College of Physicians, England (1999).

Guggenmos, J., et al., "Antibody Cross-Reactivity between Myelin Oligodendrocyte Glycoprotein and the Milk Protein Butyrophilin in Multiple Sclerosis," *J. Immunol. 172*:661-668, The American Association of Immunologists, Inc., United States (2004).

Hemmer, B., et al, "Cytokine Phenotype of Human Autoreactive T Cell Clones Specific for the Immunodominant Myelin Basic Protein Peptide (83-99)," *J. Neurosci. Res. 45*:852-862, Wiley-Liss, Inc., United States (1996).

Hintzen, R.Q. and Polman, C.H., "Th-cell modulation in multiple sclerosis," *Immunol. Today 18*(10):507-508, Elsevier/North-Holland Biomedical Press, England (1997).

Hohenegger, M., et al., "Nephrotoxicity of Fumaric Acid Monoethylester (FA ME)," *Advances in Experimental Medicine and Biology 252*:265-272, Kluwer Academic, United States (1989).

Hultgren, B., et al., "Genetic Absence of γ-Interferon Delays but Does Not Prevent Diabetes in NOD Mice," *Diabetes 45*:812-817, American Diabetes Association, United States (1996).

English language excerpt from Hunziker, T. and Schmidli, J., "Is Psoriasis an.Autoimmune Disease?" *Therapeutische Umschau 50*:110-113, Determatologische Klinik der Universitdt Bern, Switzerland (1993).

Hunziker, T. and Schmidli, J., "Psoriasis, eine Autoimmunkrankheit?" *Therapeutische Umschau 50*:110-113, Determatologische Klinik der Universität Bern, Switzerland (1993).

Issazadeh, S., et al., "Cytokine production in the central nervous system of Lewis rats with experimental autoimmune encephalomyelitis: dynamics of mRNA expression for interleukin-10, interleukin-12, cytolysin, tumor necrosis factor α and tumor necrosis factor β," *J. Neuroimmunol. 61*:205-212, Elsevier Science B.V, Netherlands (1995).

Issazadeh, S., et al., "Interferon γ, Interleukin 4 and Transforming Growth Factor β in Experimental Autoimmune Encephalomyelitis in Lewis Rats: Dynamics of Cellular mRNA Expression in the Central Nervous System and Lymphoid Cells," *J. Neurosci. Res. 40*:579-590, Wiley-Liss, Inc., United States (1995).

Issazadeh, S., et al., "Cytokines in relapsing experimental autoimmune encephalomyelitis in DA rats: persistent mRNA expression of proinflammatory cytokines and absent expression of interleukin-10 and transforming growth factor-β," *J. Neuroimmunol. 69*:103-115, Elsevier Science B.V Netherlands (1996).

Issazadeh, S., et al., "Major histocompatibility complex-controlled protective influences on experimental autoimmune encephalomyelitis are peptide specific," *Eur. J. Immunol. 27*:1584-1587, VCH Verlagsgeseelschaft mbH, Germany (1997).

Kappos, L., et al., "Efficacy and safety of oral fumarate in patients with relapsing-remitting multiple sclerosis: a multicentre, randomised, double-blind, placebo-controlled phase IIb study," *Lancet 372*:1463-1472, Lancet Publishing Group., England (2008).

Khademi, M., et al., "Induction of systemic TNFα in Natalizumab-treated multiple sclerosis," *Eur. J. Neurol. 15*:309-312, European Federation of Neurological Sciences, England (2008).

Khademi, M., et al., "Reduction of both pro- and anti-inflammatory cytokines after 6 months of interferon beta-1a treatment of multiple sclerosis," *J. Neuroimmunol. 103*:202-210, Elsevier Science B.V., Netherlands (2000).

Khademi, M., et al., "T Cell Ig- and Mucin-Domain-Containing Molecule-3 (TIM-3) and TIM-1 Molecules Are Differentially Expressed on Human Th1 and Th2 Cells and in Cerebrospinal Fluid-Derived Mononuclear Cells in Multiple Sclerosis," *J. Immunol. 172*:7169-7176, The American Association of Immunologists, Inc., United States (2004).

Kiehl, R. and Ionescu, G., "A Defective Purine Nucleotide Synthesis Pathway in Psoriatic Patients," *Acta Derm. Venereol.* (Stockh) 72:253-255, Society for the Publication of Acta Dermato-Venerologica, Sweden (1992).

Kjellén, P., et al., "Genetic influence on disease course and cytokine response in relapsing experimental allergic encephalomyelitis," *Int. Immunol. 10*:333-340, Oxford University Press, England (1998).

Kolbach, D.N. and Nieboer, C., "Fumaric acid therapy in psoriasis: Results and side effects of 2 years of treatment," *J. Am. Acad. Derm. 27*(5):769-771, Mosby, United States (1992).

Krakauer, M., et al., "Dynamic T-lymphocyte Chemokine Receptor Expression Induced by Interferon-beta Therapy in Multiple Sclerosis," *Scand. J. Immunol. 64*:155-163, Blackwell Publishing Ltd., England (2006).

Krakowski, M. and Owens, T., "Interferon-γ confers resistance to experimental allergic encephalomyelitis," *Eur. J. Immunol. 26*:1641-1646, VCH Verlagsgesellschaft mbH, Germany (1996).

Kuroda, K., et al., "Fumaric Acid Enhances DNA Synthesis of Rat Hepatocytes by Counteracting the Toxicities of Mitomycin C and Aflatoxin $B_1$," *Jpn. J. Cancer Res. (Gann) 77*:750-758, Japanese Cancer Association, Japan (1986).

LaFaille, J.J., et al., "Myelin Basic Protein-specific T Helper 2 (Th2) Cells Cause Experimental Autoimmune Encephalomyelitis in Immunodeficient Hosts Rather than Protect Them from the Disease," *J. Exp. Med. 186*(2):307-312, The Rockefeller University Press, United States (1997).

LaFaille, J.J., "The Role of Helper T Cell Subsets in Autoimmune Diseases," *Cytokine & Growth Factor Rev. 9*(2):139-151, Elsevier Science Ltd., England (1998).

Lahti, A. and Maibach, H.I., "Contact urticaria from diethyl fumarate," *Contact Dermatitis 12*:139-140, Munksgaard, Denmark (1985).

Laman, J.D., et al., "Balancing the Th1/Th2 concept in multiple sclerosis," *Immunol. Today 19*(11):489-490, Elsevier/North-Holland Biomedical Press, England (1998).

Lehnert, S., et al., "Radiation Response of Drug-Resistant Variants of a Human Breast Cancer Cell Line: The Effect of Glutathione Depletion," *Radiation Res. 124*:208-215, Academic Press, Inc., United States (1990).

Liedtke, W., et al., "Effective Treatment of Models of Multiple Sclerosis by Matrix Metalloproteinase Inhibitors," *Ann. Neurol. 44*(1):35-46, The American Neurological Association, United States (1998).

Link, J., et al., "Organ-specific autoantigens induce interferon-γ and interleukin-4 mRNA expression in mononuclear cells in multiple sclerosis and myasthenia gravis," *Neurology* 44:728-734, The American Academy of Neurology, United States (1994).

Link, J., et al., "Organ-specific Autoantigens Induce Transforming Growth Factor-β mRNA Expression in Mononuclear Cells in Multiple Sclerosis and Myasthenia Gravis," *Annals Neurol.* 35:197-203, The American Neurological Association, United States (1994).

Link, J., et al., "Optic neuritis is associated with myelin basic protein and proteolipid protein reactive cells producing interferon-γ, interleukin-4 and transforming growth factor-β," *J. Neuroimmunol.* 49:9-18, Elsevier Science B.V., Netherlands (1994).

Link, J., et al., "Increased Transforming Growth Factor-β, Interleukin-4, and Interferon-γ in Multiple Sclerosis," *Ann. Neurol.* 36(3):379-386, The American Neurological Association, United States (1994).

Link, H., "The cytokine storm in multiple sclerosis," *Mult. Scler.* 4:12-15, Stockton Press, England (1998).

Linker, R.A., et al., "Fumarates for the treatment of multiple sclerosis: potential mechanisms of action and clinical studies," *Expert Rev. Neurother.* 8(11):1683-1690, Expert Reviews Ltd., England (2008).

Lobell, A., et al., "Suppressive DNA Vaccination in Myelin Oligodendrocyte Glycoprotein Peptide-Induced Experimental Autoimmune Encephalomyelitis Involves a T1-Biased Immune Response," *J. Immunol.* 170:1806-1813, The American Association of Immunologists, Inc., United States (2003).

Lobell, A., et al., "Vaccination with DNA Encoding an Immunodominant Myelin Basic Protein Peptide Targeted to Fc of Immunoglobulin G Suppresses Experimental Autoimmune Encephalomyelitis," *J. Exp. Med.* 187(9):1543-1548, The Rockefeller University Press, United States (1998).

Lopez, E., et al., "Interferon γ, IL2, IL4, IL10 and TNFα Secretions in Multiple Sclerosis Patients Treated with an Anti-CD4 Monoclonal Antibody," *Autoimmunity* 29:87-92, OPA (Overseas Publishers Association) N.V., England (1999).

Lorentzen, J.C., et al., "Genetic analysis of inflammation, cytokine mRNA expression and disease course of relapsing experimental autoimmune encephalomyelitis in DA rats," *J. Neuroimmunol.* 80:31-37, Elsevier Science N.V., Netherlands (1997).

Lorentzen, J.C., et al., "Protracted, relapsing and demyelinating experimental autoimmune encephalomyelitis in DA rats immunized with syngeneic spinal cord and incomplete Freund's adjuvant," *J. Neuroimmunol.* 63:193-205, Elsevier Science B.V., Netherlands (1995).

Lyons, J.-A., et al., "Pathogenesis of acute passive murine encephalomyelitis II. Th1 phenotype of the inducing population is not sufficient to cause disease," *J. Neuroimmunol.* 93:26-36, Elsevier Science B.V., Netherlands (1999).

Määttä, J.A., et al., "Neutrophils secreting tumor necrosis factor alpha infiltrate the central nervous systems of BALB/c mice with experimental autoimmune encephalomyelitis," *J. Neuroimmunol.* 90:162-175, Elsevier Science B.V., Netherlands (1998).

Martin, R., et al., "T helper cell differentiation in multiple sclerosis and autoimmunity," *Immunol. Today* 19(11):495-498, Elsevier Science, England (1998).

Mattner, F., et al., "Inhibition of Th1 development and treatment of chronic-relapsing experimental allergic encephalomyelitis by a non-hypercalcemic analogue of 1,25-dihydroxyvitamin $D_3$," *Eur. J. Immunol.* 30:498-508, Wiley-VCH Verlag GmbH, Germany (2000).

Matusevicius, D., et al., "Autoantigen-induced IL-13 mRNA expression is increased in blood mononuclear cells in myasthenia gracis and multiple sclerosis," *Eur. J. Neurol.* 4:468-475, Rapid Science Publisher, England (1997).

Asadullah, K., et al., "Influence of monomethylfumarate on monocytic cytokine formation—explanation for adverse and therapeutic effects in psoriasis?" *Arch. Dermatol. Res.* 289:623-630, Springer-Verlag, Germany (1997).

Bacharach-Buhles, M., et al., "The Effect of Fumaric Acid Esters and Dithranol on Acanthosis and Hyperproliferation in *Psoriasis vulgaris*," *Acta Derm. Venereol.* (Stockh) 76:190-193, Scandinavian University Press, Sweden (1996).

Balashov, K.E., et al., "Increased interleukin 12 production in progressive multiple sclerosis: Induction by activated $CD4^+$ T cells via CD40 ligand," *Proc. Natl. Acad. Sci. USA* 94:599-603, The National Academy of Sciences of the United States of America, United States (1997).

Barcia, C., et al., "Parkinson's Disease and Inflammatory Changes," *Neurotox. Res.* 5(6):411-418, FP Graham Publishing Co., United States (2003).

Breuer, K., et al., "Therapy of noninfectious granulomatous skin diseases with fumaric acid esters," *Br. J. Dermatol.* 152:1290-1295, British Association of Dermatologists, England (2005).

Eberlein-König, B., et al., "Disseminated Granuloma Annulare—Treatment with Fumaric Acid Esters," *Dermatology* 210:223-226, S. Karger AG, Switzerland (2005).

Link, H., et al., "Virus-reactive and autoreactive T cells are accumulated in cerebrospinal fluid in multiple sclerosis," *J. Neuroimmunol.* 38:63-74, Elsevier Science Publishers B.V., Netherlands (1992)

Litjens, N.H.R., et al., "Monomethylfamarate affects polarization of monocyte-derived dendritic cells resulting in down-regulated Th1 lymphocyte responses," *Eur. J Immunol.* 34:565-575, Wiley-VCH Verlag GmbH & Co. KGaA, Germany (2004).

Litjens, N.H.R., et al., "Pharmacokinetics of oral fumarates in healthy subjects," *Br. J. Clin. Pharmacol.* 58(4):429-432, Blackwell Publishing Ltd, England (2004).

Lobell, A., et al., "Presence of CpG DNA and the Local Cytokine Milieu Determine the Efficacy of Suppressive DNA Vaccination in Experimental Autoimmune Encephalomyelitis," *J. Immunol.* 163:4754-4762, The American Association of Immunologists, United States (1999).

Loewe, R., et al., "Dimethylfumarate Inhibits TNF-Induced Nuclear Entry of NF-κKb/p65 in Human Endothelial Cells," *J. Immunol.* 168:4781-4787, The American Association of Immunologists, United States (2002).

Luft, R., "The development of mitochondrial medicine," *Proc. Natl. Acad. Sci. USA* 91:8731-8738, National Academy of Sciences, United States (1994).

Mayne, M., et al., "Antisense Oligodeoxynucleotide Inhibition of Tumor Necrosis Factor-α Expression is Neuroprotective After Intracerebral Hemorrhage," *Stroke* 32:240-248, American Heart Association, Inc., United States (2001).

McGeer, P.L., et al., "Expression of the histocompatibility glycoprotein HLA-DR in neurological disease," *Acta Neuropathol.* 76:550-557, Springer-Verlag, Germany (1988).

Muhallab, S., et al., "Intra-CNS activation by antigen-specific T lymphocytes in experimental autoimmune encephalomyelitis," *J. Neuroimmunol.* 113:202-211, Elsevier Science B.V., Netherlands (2001).

Musiek, E.S., et al., "Cyclopentenone isoprostanes are novel bioactive products of lipid oxidation which enhance neurodegeneration," *J. Neurochem.* 97:1301-1313, International Society for Neurochemistry, England (2006).

Mustafa, M.I., et al., "T cell immunity and interferon-γ secretion during experimental allergic encephalomyelitis in Lewis rats," *J. Neuroimmunol.* 31:165-177, Elsevier Science Publishers B.V., Netherlands (1991).

Mustafa, M., et al., "Immunopharmacologic Modulation of Experimental Allergic Encephalomyelitis: Low-Dose Cyclosporin—A Treatment Causes Disease Relapse and Increased Systemic T and B Cell-Mediated Myelin-Directed Autoimmunity," *Scand. J. Immunol.* 38:499-507, Blackwell Scientific Publications, England (1993).

Mustafa, M., et al., "The major histocompatibility complex influences myelin basic protein 63-88-induced T cell cytokine profile and experimental autoimmune encephalomyelitis," *Eur. J. Immunol.* 23:3089-3095, VCH Verlagsgesellschaft mbH, Germany (1993).

Mustafa, M., et al., "Protective Influences on Experimental Autoimmune Encephalomyelitis by MHC Class I and Class II Alleles," *J. Immunol.* 153:3337-3344, The American Association of Immunologists, United States (1994).

Navikas, V., et al., "Increased mRNA Expression of IL-10 in Mononuclear Cells in Multiple Sclerosis and Optic Neuritis," *Scand. J. Immunol.* 41:171-178, Blackwell Scientific Publications, England (1995).

Navikas, V., et al., "Augmented expression of tumour necrosis factor-α and lymphotoxin in mononuclear cells in multiple sclerosis and optic neuritis," *Brain* 119:213-223, Oxford University Press, England (1996).

Nibbering, P.H., et al., "Effects of Monomethylfumarate on Human Granulocytes," *J. Invest. Dermatol. 101*:37-42, The Society for Investigative Dermatology, Inc., United States (1993).

Nibbering, P.H., et al., "Intracellular signalling by binding sites for the antipsoriatic agent monomethylfumarate on human granulocytes," *Br. J. Dermatol. 137*:65-75, British Association of Dermatologists, England (1997).

Nieboer, C., et al., "Systemic therapy with fumaric acid derivates: New possibilities in the treatment of psoriasis," *J. Am. Acad. Dermatol. 20*:601-608, Mosby, United States (1989).

Ockenfels, H.M., et al., "The antipsoriatic agent dimethylfumarate immunomodulates T-cell cytokine secretion and inhibits cytokines of the psoriatic cytokine network," *Br. J. Dermatol. 139*:390-395, British Association of Dermatologists, England (1998).

Olsson, T., et al., "Autoreactive T Lymphocytes in Multiple Sclerosis Determined by Antigen-induced Secretion of Interferon-γ," *J. Clin. Invest. 86*:981-985, The American Society for Clinical Investigation, Inc., United States (1990).

Olsson, T., "Cytokines in neuroinflammatory disease: role of myelin autoreactive T cell production of interferon-gamma," *J. Neuroimmunol. 40*:211-218, Elsevier Science Publishers B.V., Netherlands (1992).

Olsson, T., et al., "Increased numbers of T cells recognizing multiple myelin basic protein epitopes in multiple sclerosis," *Eur. J. Immunol. 22*:1083-1087, VCH Verlagsgesellschaft mbH, Germany (1992).

Olsson, T., "Cerebrospinal Fluid," *Ann. Neurol. 36*:S100-S102, American Neurological Association, United States (1994).

Olsson, T., "Role of cytokines in multiple sclerosis and experimental autoimmune encephalomyelitis," *Eur. J. Neurol. 1*:7-19, Rapid Communications of Oxford Ltd., England (1994).

Olsson, T., "Cytokine-producing cells in experimental autoimmune encephalomyelitis and multiple sclerosis," *Neurology 45*(Suppl 6):S11-S15, Lipincott Williams & Wilkins, United States (1995).

Olsson, T., et al., "Genetics of rat neuroinflammation," *J. Neuroimmunol. 107*:191-200, Elsevier Science B.V., Netherlands (2000).

Olsson, T., et al., "Depletion of Vβ5.2/5.3 T cells with a humanized antibody in patients with multiple sclerosis," *Eur. J. Neurol. 9*:153-164, European Federation of Neurological Societies, England (2002).

Olsson, T., et al., "Harm or heal—divergent effects of autoimmune neuroinflammation?" *TRENDS in Immunol. 24*(1):5-6, Elsevier Science Ltd., England (2003).

Panitch, H.S., et al., "Exacerbations of Multiple Sclerosis in Patients Treated With Gamma Interferon," *Lancet 329*:893-895, Lancet Publishing Group, England (1987).

Pereira, M.A., et al., "Use of azoxymethane-induced foci of aberrant crypts in rat colon to identify potential cancer chemopreventive agents," *Carcinogenesis 15*(5):1049-1054, Oxford University Press, England (1994).

Pette, M., et al., "Differential effects of phosphodiesterase type 4-specific inhibition on human autoreactive myelin-specific T cell clones," *J. Neuroimmunol 98*:147-156, Elsevier Science B.V., Netherlands (1999).

Prochaska, H.J., et al., "Elevation of Glutathione Levels by Phase II Enzyme Inducers: Lack of Inhibition of Human Immunodeficiency Virus Type 1 Replication in Chronically Infected Monocytoid Cells," *Mol. Pharmacol. 45*:916-921, The American Society for Pharmacology and Experimental Therapeutics, United States (1994).

Rao, C.V., et al., "Chemoprevention of Azoxymethane-Induced Colon Cancer by Ascorbylpalmitate, Carbenoxolone, Dimethylfumarate and p-Methoxyphenol in Male F344 Rats," *Anticancer Res. 15*:1199-1204, Anticancer Research, Greece (1995).

Rao, K.S. and Mishra, S.H., "Antihepatotoxic activity of monomethyl fumarate isolated from *Fumaria indica*," *J. Ethnopharmacol. 60*:207-213, Elsevier Science Ireland Ltd., Ireland (1998).

Ristori, G., et al., "T cell response to myelin basic protein before and after treatment with interferon beta in multiple sclerosis," *J. Neuroimmunol. 99*:91-96, Elsevier Science B.V., Netherlands (1999).

Robinson, W.H., et al., "Protein microarrays guide tolerizing DNA vaccine treatment of autoimmune encephalomyelitis," *Nat. Biotechnol. 21*(9):1033-1039, Nature Publishing Group, United States (2003).

Rohowsky-Kochan, C., et al., "Impaired interleukin-12 production in multiple sclerosis patients," *Mult. Scler. 5*:327-334, Stockton Press, England (1999).

Rohowsky-Kochan, C., et al., "Cytokine secretion profile of myelin basic protein-specific T cells in multiple sclerosis," *Mult. Scler. 6*:69-77, Macmillan Publishers Ltd., England (2000).

Romagnani, S., "The Th1/Th2 paradigm," *Immunol. Today 18*(6):263-266, Elsevier Science Ltd., England (1997).

Rook, G.A.W., et al., "Bacterial vaccines for the treatment of multiple sclerosis and other autoimmune diseases," *Immunol. Today 21*(10):503-508, Elsevier Science Ltd., in 190:83-89, England (2000).

Samoilova, E.B., et al., "Experimental Autoimmune Encephalomyelitis Intercellular Adhesion Molecule-1-Deficient Mice," *Cell. Immunol. 190*:83-89, Academic Press, United States (1998).

Sebök, B., et al., "Antiproliferative and cytotoxic profiles of antipsoriatic fumaric acid derivatives in keratinocyte cultures," *Eur. J. Pharmacol. 270*:79-87, Elsevier Science B.V., Netherlands (1994).

Sebök, B., et al., "Effect of Fumaric Acid, Its Dimethylester, and Topical Antipsoriatic Drugs on Epidermal Differentiation in the Mouse Tail Model," *Skin Pharmacol. 9*:99-103, S. Karger AG, Switzerland (1996).

Singh, V.K., et al., "The Paradigm of Th1 and Th2 Cytokines. Its Relevance to Autoimmunity and Allergy," *Immunol. Res. 20*:147-161, Humana Press Inc., United States (1999).

Sinigaglia, F., et al., "Type I interferons and the Th1/Th2 paradigm," *Dev. Comp. Immunol. 23*:657-663, Elsevier Science Ltd., United States (1999).

Smeltz, R.B. and Swanborg, R.H., "Concordance and Contradiction Concerning Cytokines and Chemokines in Experimental Demyelinating Disease," *J. Neurosci. Res. 51*:147-153, Wiley-Liss, Inc., United States (1998).

Söderström, M., et al., "T Cells Recognizing Multiple Pepties of Myeline Basic Protein are Found in Blood and Enriched in Cerebrospinal Fluid in Optic Neuritis and Multiple Sclerosis," *Scand. J. Immunol. 37*:355-368, Blackwell Scientific Publications, England (1993).

Spencer, S.R., et al., "Induction of Glutathione Transferases and NAD(P)H:Quinone Reductase by Fumaric Acid Derivatives in Rodent Cells and Tissues," *Cancer Res. 50*:7871-7875, American Association for Cancer Research, United States (1990).

Su, J.Y.C., et al., "Reduction of $H_2O_2$-evoked, intracellular calcium increases in the rat N18-RE-105 neuronal cell line by pretreatment with an electrophilic antioxidant inducer," *Neurosci. Lett. 273*:109-112, Elsevier Science Ireland Ltd., Ireland (1999).

Sun, J.-B., et al., "Treatment of experimental autoimmune encephalomyelitis by feeding myelin basic protein conjugated to cholera toxin B subunit," *Proc. Natl. Acad. Sci. USA 93*:7196-7201, National Academy of Sciences, United States (1996).

Thio, H.B., et al., "Fumaric acid derivatives evoke a transient increase in intracellular free calcium concentration and inhibit the proliferation of human keratinocytes," *Brit. J. Dermatol. 131*:856-861, Blackwell Scientific Publications, England (1994).

Venten, I., et al., "Treatment of Therapy-Resistant Alopecia Areata With Fumaric Acid Esters," *Eur. J. Med Res. 11*:300-305, I. Flolzapfel Publishers, Germany (Jul. 2006).

Wallström, E., et al., "Memantine abrogates neurological deficits, but not CNS inflammation, in Lewis rat experimental autoimmune encephalomyelitis," *J. Neurol. Sci. 137*:89-96, Elsevier Science B.V., Netherlands (1996).

Wallström, E., et al., "Increased reactivity to myelin oligodendrocyte glycoprotein peptides and epitope mapping in HLA DR2(15)+ multiple sclerosis," *Eur. J. Immunol. 28*:3329-3335, Wiley-VCH Verlag GmbH, Germany (1998).

Wang, W.Z., et al., "Myelin antigen reactive T cells in cerebrovascular diseases," *Clin. Exp. Immunol. 88*:157-162, Blackwell Scientific Publications, England (1992).

Weissert, R., et al., "Protective DNA vaccination against organ-specific autoimmunity is highly specific and discriminates between single amino acid substitutions in the peptide autoantigen," *Proc. Natl. Acad. Sci. USA 97*(4):1689-1694, National Academy of Sciences, United States (2000).

Wright, R., "Autoimmune disease of the gastro-intestinal tract," *Postgrad. med. J. 44*:765-768, BMJ Publishing Group, England (1968).

Zhu, J., et al., "Cytokine production and the pathogenesis of experimental autoimmune neuritis and Guillain-Barré syndrome," *J. Neuroimmunol. 84*:40-52, Elsevier Science B.V., Netherlands (1998).

Zipp, F., "No Evidence for Generation of Th-2-like MBP-Specific T-Cell Lines by Blockade of the Costimulatory Molecule B7-1," *Scand. J. Immunol. 52*:510-514, Blackwell Science Ltd., England (2000).

Alexander, A. and Wong, S., "Graft Versus Host Disease—Pathophysiology & Management," *Jacksonville Medicine: Bone Marrow Transplantation 51*(11):1-7, Duval County Medical Society Foundation for the Duval, Clay, Nassau, St. Johns & Putnam Medical Societies, United States (2000).

Anderson, J., et al., "Aetiology of Multiple Sclerosis," *Br. Med. J 1*(5433):466-467, British Medical Association, England (1965).

Brochet, B., "[Non-specific immunosuppression and multiple sclerosis]," *Rev. Abs. Neurol.* (Paris) 154(8-9):629-634, Masson, France (1998) (Abstract Only).

Calabrese, V., et al., "Acetylcarnitine Induces Heme Oxygenase in Rat Astrocytes and Protects Against Oxidative Stress: Involvement of the Transcription Factor Nrf2," *J. Neurosci. Res. 79*:509-521, Wiley-Liss, Inc., United States (2005).

Chen, X.L. and Kunsch, C., "Induction of Cytoprotective Genes Through Nrf2/Antioxidant Response Element Pathway: A New Therapeutic Approach for the Treatment of Inflammatory Diseases," *Curr. Pharm. Des. 10*:879-891, Bentham Science Publishers Ltd., Netherlands (2004).

Coras, B., et al., "Fumaric acid esters therapy: a new treatment modality in pityriasis rubra pilaris?" *Br. J. Dermatol. 152*:388-389, British Association of Dermatologists, England (2005).

Fox, R.I., "BG00012—Novel Oral Therapy in Development for the Treatment of Multiple Sclerosis," *European Neurological Review 3*(1):99-103, Touch Briefings, England (2008).

Gambichler, T., et al., "Clearance of Necrobiosis lipoidica with Fumaric Acid Esters," *Dermatology 207*(4):422-424, S. Karger AG, Switzerland (2003).

Gao, L., et al., "Novel N-3 Fatty Acid Oxidation Products Activate Nrf2 by Destabilizing the Association Between Keap1 and Cullin3," *J. Biol. Chem. M607622200*, 18 pages, The American Society for Biochemistry and Molecular Biology, Inc., United States (Nov. 2006).

Gilgun-Sherki, Y., et al., "The role of oxidative stress in the pathogensis of multiple sclerosis: The need for effective antioxidant therapy," *J. Neurol. 251*:261-268, Springer-Verlag, Germany (2004).

Graves, M.C., et al., "Inflammation in amyotrophic lateral sclerosis spinal cord and brain is mediated by activated macrophages, mast cells and T cells," *Amyotroph. Lateral Scler. Other Motor Neuron Disord. 5*:213-219, Martin Dunitz, England (2004).

Gutzmer, R., et al., "Erfolgreiche Therapie einer Haut- und Lungensarkoidose mit Fumarsäureestern," *Hautarzt 55*:553-557, Springer-Verlag, Germany (2004).

Gutzmer, R., et al., "[Successful treatment of skin and lung sarcoidosis with fumaric acid ester].," *Hautarzt 55*:553-557, Springer-Verlag, Germany (2004) (Abstract Only).

Hagedorn, M., et al., "Therapie der rezidivierenden benignen Aphthosis mit Fumarsäureestern," *Akt. Dermatol. 31*:383-387, Georg Thieme Verlag KG, Germany (2005) (Abstract Only in English).

Kensler, T.W., et al., "Cell Survival Responses to Environmental Stresses Via the Keap1-Nrf2-ARE Pathway," *Annu. Rev. Pharmocol. Toxicol. 47*:6.1-6.28, Annual Reviews, United States (2007; Epub Aug. 2006).

Kreuter, A., et al., "Treatment of disseminated granuloma annulare with fumaric acid esters," *BMC Dermatol. 2*(5):1-4, BioMed Central Ltd., England (2002).

Kreuter, A., et al., "Fumaric acid esters in necrobiosis lipoidica: results of a prospective noncontrolled study," *Br. J. Dermatol. 153*:802-807, British Association of Dermatologists, England (2005).

Kwak, M.-K., et al., "Enhanced Expression of the Transcription Factor Nrf2 by Cancer Chemopreventive Agents: Role of Antioxidant Response Element-Like Sequences in the *nrf2* Promoter," *Mol. Cell Biol. 22*(9):2883-2892, American Society for Microbiology, United States (2002).

Kwak, M.-K., et al., "Modulation of Gene Expression by Cancer Chemopreventive Dithiolethiones through the Keap1-Nrf2 Pathway," *J. Biol. 278*(10):8135-8145, The American Society for Biochemistry and Molecular Biology, Inc., United States (2003).

Lahti, A., et al., "Acetylsalicylic acid inhibits non-immunologic contact urticaria," *Contact Dermatitis 16*:133-135, Munksgaard International Publishers Ltd., Denmark.

Lee, J.-M., et al., "Identification of the NF-E2-related Factor-2-dependent Genes Conferring Protection against Oxidative Stress in Primary Cortical Astrocytes Using Oligonucleotide Microarray Analysis," *J. Biol. Chem. 278*(14):12029-12038, The American Society for Biochemistry and Molecular Biology, Inc., United States (2003).

Lehmann, J.C.U., et al., "Dimethylfumarate Induces Immunosuppression *via* Glutathione Depletion and Subsequent Induction of Heme Oxygenase 1," *J. Invest. Dermatol. 127*:835-845, The Society for Investigative Dermatology, United States (Epub Jan. 18, 2007).

Liang, Q., et al., "Noninvasive, Repetitive, Quantitative Measurement of Gene Expression from a Bicistronic Message by Positron Emission Tomography, Following Gene Transfer with Adenovirus," *Mol. Ther. 6*(1):73-82, The American Society of Gene Therapy, United States (2002).

Luker, G.D., et al., "Noninvasive Bioluminescence Imaging of Herpes Simplex Virus Type 1 Infection and Therapy in Living Mice," *J Virol. 76*(23):12149-12161, American Society for Microbiology, United States (2002).

Ma, Q., et al., "Multiorgan Autoimmune Inflammation, Enhanced Lymphoproliferation, and Impaired Homeostasis of Reactive Oxygen Species in Mice Lacking the Antioxidant-Activated Transcription Factor *Nrf2*," *Am. J Pathol. 168*(6):1960-1974, American Society for Investigative Pathology, United States (Jun. 2006).

Mattson, M.P. and Cheng, A., "Neurohormetic phytochemicals: low-dose toxins that induce adaptive neuronal stress responses," *TRENDS in Neurosciences 29*(11):632-639, Elsevier Ltd., England (Sep. 2006).

Nguyen, T., et al.,"Nrf2 Controls Constitutive and Inducible Expression of ARE-driven Genes through a Dynamic Pathway Involving Nucleocytoplasmic Shuttling by Keap1," *J. Biol. Chem. 280*(37):32485-32492, The American Society for Biochemistry and Molecular Biolou, Inc., United States (2005).

Nieboer, C., et al., "Fumaric Acid Therapy in Psoriasis: A Double-Blind Comparison between Fumaric Acid Compound Therapy and Monotherapy with Dimethylfumaric Acid Ester," *Dermatologica 181*:33-37, Karger AG, Switzerland (1990).

Nowack, U., et al., "Successful treatment of recalcitrant cutaneous sarcoidosis with fumaric acid esters," *BMC Dermatol.2*(15):1-5, BioMed Central Ltd., England (2002).

O'Garra, A., et al., "CD4+ T-cell subsets in autoimmunity," *Curr. Opin. Immunol. 9*:872-883, Current Biology Ltd., England (1997).

Olsson, T., et al., "Chapter 22: MHC and Non-MHC Genetics of Experimental Autoimmune Encephalomyelitis," in *From Basic Immunology to Immune-Mediated Demyelination*, Martino, G. and Adorini, L., eds., p. 246-264, Springer-Verlag, Italy (1999).

Olsson, T., "Critical Influences of the Cytokine Orchestration on the Outcome of Myelin Antigen-Specific T-Cell Autoimmunity in Experimental Autoimmune Encephalomyelitis and Multiple Sclerosis," *Immunol. Rev. 144*:245-268, Munksgaard, Denmark (1995).

Pashenkov, M., et al., "Recruitment of dendritic cells to the cerebrospinal fluid in bacterial neuroinfections," *J. Neuroimmunol. 122*:106-116, Elsevier Science B.V., Netherlands (2002).

Permana, P.A., et al., "Macrophage-secreted factors induce adipocyte inflammation and insulin resistance," *Biochem. Biophys. Res. Commun. 341*:507-514, Elsevier Inc., United States (Epub Jan. 2006).

Pette, M., et al., "In vitro modulation of human, autoreactive MBP-specific CD4 + T-cell clones by cyclosporin A," *J. Neuroimmunol.* 76:91-99, Elsevier Science B.V., Netherlands (1997).

Roodnat, J.I., et al., "Akute Niereninsuffizienz bei der Behandlung der Psoriasis mit Fumasäure-Estern," *Schweiz. med. Wschr.* 119:826-830, Basel, B. Schwabe & Abs. Co., Switzerland (1989) (Abstract Only in English).

Rudge, P., "Cyclosporine and multiple sclerosis: The cons," *Neurology* 38(7)(Suppl 2):29-30, Lippincott Williams & Wilkins, United States (1988).

Ruuls, S.R., et al., "The Length of Treatment Determines Whether IFN-β Prevents or Aggravates Experimental Autoimmune Encephalomyelitis in Lewis Rats," *J. Immunol.* 157:5721-5731, The American Association of Immunologists, United States (1996).

Satoh, T., et al., "Activation of the Keap1/Nrf2 pathway for neuroprotection by electrophillic phase II inducers," *Proc. Natl. Acad. Sci. USA* 103(3):768-773, The National Academy of Sciences of the USA, United States (Jan. 2006).

Schilling, F. and Schopf, R.E., "Adultes Debré-de Toni-Fanconi-Syndrom mit Osteomalazie, erworben durch Langzeittherapie einer Psoriasis mit Fumarsäureester—zugleich ein Beitrag zur malazischen Osteoarthropathie," *Akt. Rheumatol.* 24(6):174-179, Georg Thieme Verlag, Germany (1999) (Abstract Only in English).

Schilling, S., et al., "Fumaric acid esters are effective in chronic experimental autoimmune encephalomyelitis and suppress macrophage infiltration," *Clin. Exp. Immunol.* 145:101-107, British Society for Immunology, England (2006).

Schwinghammer, T.L. and Bloom, E.J., "Pharmacologic prophylaxis of acute graft-versus-host disease after allogeneic marrow transplantation," *Clinical Pharm.* 12:736-761, American Society of Hospital Pharmacists, Inc., United States (1993).

Shih, A.Y., et al., "A Small-Molecule-Inducible Nrf2-Mediated Antioxidant Response Provides Effective Prophylaxis against Cerebral Ischemia in Vivo," *J. Neurosci.* 25(44):10321-10335, Society for Neuroscience, United States (2005).

Summers, S.A., "Ceramides in insulin resistance and lipotoxicity," *Prog. Lipid Res.* 45:42-72, Elsevier Ltd., England (Jan. 2006; Epub Dec. 2005).

Thimmulappa, R.K., et al., "Nrf2 is a critical regulator of the innate immune response and survival during experimental sepsis," *J. Clin. Invest.* 116(4):984-995, American Society for Clinical Investigation, United States (Apr. 2006).

Van Horssen, J., et al., "NAD(P)H:quinone oxidoreductase 1 expression in multiple sclerosis lesions," *Free Radic. Biol. Med.* 41:311-317, Elsevier inc., United States (Epub Apr. 2006).

Van Loenen, A.C., et al., "Funnaarzuurtherapie: van fictie tot work werkelijkheid?" *J. Pharm. Weekbl.* 124:894-900, D B Centens Witgeversmij, Netherlands (1989) (Abstract Only in English).

Vandermeeren, M., et al., "Dimethylfumarate is an Inhibitor of Cytolcine-Induced E-Selection, VCAM-1, and ICAM-1 Expression in Human Endothelial Cells," *Biochem. Biophys. Res. Comm.* 234:19-23, Academic Press, United States (1997).

Vandermeeren, M., et al., "Dimethylfumarate is an Inhibitor of Cytokine-Induced Nuclear Translocation of NF-κB1, But Not Re1A in Normal Human Dermal Fibroblast Cells," *J. Invest. Dermatol.* 116:124-130, The Society for Investigative Dermatology, Inc., United States (2001).

Wakabayashi, N., et al., "*Keap1*-null mutation leads to postnatal lethality due to constitutive Nrf2 activation," *Nat. Genet.* 35(3):238-245, Nature Publishing Group, United States (2003).

Wanscher, B. and Sørensen, P.S., "Nye behandlingsmuligheder for dissemineret sklerose?" *Ugeskr Læger* 156(43):6353-6358, Den Alm Danske Laegerforening, Denmark (1994) (Abstract Only in English).

Werdenberg, D., et al., "Presystemic Metabolism and Intestinal Absorption of Antipsoriatic Fumaric Acid Esters," *Biopharm. Drug Dispos.* 24(6):259-273, John Wiley & Sons, Ltd., England (2003).

Werdenberg, D., *Stability, Permeability and Pharmacokinetics of Perorally Administered Fumarates*, Doctoral Dissertation submitted to the Swiss Federal Institute of Technology Zurich, pp. 86, 87, 90, 125 (2003).

Zhu, K. and Mrowietz, U., "Inhibition of Dendritic Cell Differentiation by Fumaric Acid Esters," *J Invest. Dermatol.* 116:203-208, The Society for Investigative Dermatology, Inc., United States (2001).

The Lenercept Multiple Sclerosis Study Group and the University of British Columbia MS/MRI Analysis Group, "TNF neutralization in MS: Results of a randomized, placebo-controlled multicenter study," *Neurol.* 53:457-465, American Academy of Neurology, United States (1999).

"Oral Compound BG-12 Achieves Primary Endpoint in Phase II Study of Relapsing-Remitting Multiple Sclerosis; Treatment with BG-12 Led to Statistically Significant Reductions in MRI Measures," Biogen Idec, accessed at http://phx.corporate-ir.net/staging/phoenix.zhtml?c=148682&p=irol-newsArticle_print&ID=861749&highlight, published online May 30, 2006, 2 pages.

"Phase II Study of Oral Compound BG-12 Meets Primary Endpoint in Multiple Sclerosis," Biogen Idec, accessed at http://phx.corporate-ir.net/staging/phoenix.zhtml?c=148682&p=irol-newsArticle_print&ID=801882&highlight, published online Jan. 9, 2006, 1 page.

"Polyarthritis," Wikipedia.org, accessed at www.en.wikipedia.org/wiki/Polyarthritis, accessed on Sep. 3, 2008, 4 pages.

*Immunmodulation durch Fumaderm. Das richtungsweisende Konzept*, Charite-Berlin Hautklinik Symposium, Nov. 1-3, 1996, p. 1-27.

Partial English language translation, 4 pages, of *Immunmodulation durch Fumaderm. Das richtungsweisende Konzept*, Charite-Berlin Hautklinik Symposium, Nov. 1-3, 1996, pp. 1-27.

Ando, D.G., et al., "Encephalitogenic T Cells in the B10.PL Model of Experimental Allergic Encephalomyelitis (EAE) Are of the Th-1 Lymphokine Subtype," *Cell. Immunol.* 124:132-143, Academic Press, Inc., United States (1989).

Baker, D., et al., "Induction of chronic relapsing experimental allergic encephalomyelitis in Biozzi mice," *J. Neuroimmunol.* 28(3):261-270, Elsevier Science Publishers B.V. (Biomedical Division), Netherlands, (1990).

Baxter, A.G., et al., "High and Low Diabetes Incidence Nonobese Diabetic (NOD) Mice: Origins and Characterisation," *Autoimmunity* 9:61-67, Harwood Academic Publishers GmbH, England (1991).

Bayard, W., et al., "Perorale Langzeitbehandlung der Psoriasis mit Fumarsäurederivaten" *Hautarzt* 38:279-285, Springer-Verlag, Germany (1987) (Abstract Only in English).

Ben-Nun, A., et al., "The rapid isolation of clonable antigen-specific T lymphocyte lines capable of mediating autoimmune encephalomyelitis," *Eur. J. Immunol.* 11:195-199, Verlag Chemie, GmbH, Germany (1981).

Butter, C., et al., "Mononuclear cell trafficking and plasma protein extravasation into the CNS during chronic relapsing experimental allergic encephalomyelitis in Biozzi AB/H mice," *J. Neurol. Sci.* 104:9-12, Elsevier Science Publishers B.V., Netherlands (1991).

Dinkova-Kostova, A.T., et al., "Potency of Michael reaction acceptors as inducers of enzymes that protect against carcinogenesis depends on their reactivity with sulfhydryl groups," *Proc. Natl. Acad. Sci. USA* 98(6):3404-3409, National Academy of Sciences, United States (2001).

*Encyclopedia of Molecular Biology and Molecular Medicine*, Meyers, R.A., ed., p. 343, VCH Verlagsgesellschaft mbH, Germany (1996).

Ercolinl A.M. and Miller, S.D., "Mechanisms of Immunopathology in Murine Models of Central Nervous System Demyelinating Disease," *J. Immunol.* 176(6):3293-3298, The American Association of Immunologists, Inc., United States (Mar. 2006).

Eugster, H.-P., et al., "Severity of symptoms and demyelination in MOG-induced EAE depends on TNFR1," *Eur. J. Immunol.* 29:626-632, Wiley-VCH Verlag GmbH, Germany (1999).

Freireich, E.J., et al., "Quantitative Comparison of Toxicity of Anticancer Agents in Mouse, Rat, Hamster, Dog, Monkey, and Man," *Cancer Chemother. Reports* 50(4):219-244, National Cancer Institute, United States (1966).

Friedrich, M., et al., "Addition of Pentoxifylline Could Reduce the Side Effects of Fumaric Acid Esters in the Treatment of Psoriasis," *Acta Derm. Venereol.* 81:429-430, Taylor & Francis, Sweden (2001).

Gold, R., et al., "Understanding pathogenesis and therapy of multiple sclerosis via animal models: 70 years of merits and culprits in experimental autoimmune encephalomyelitis research," *Brain* 129:1953-1971, Oxford University Press, England (Aug. 2006).

Habig, W.H., et al., "Glutathione S-Transferases: The First Enzymatic Step in Mercapturic Acid Formation," *J. Biol. Chem.* 249(22):7130-7139, The American Society for Biological Chemists, Inc., United States (1974).

Harris, J.O., et al., "Serial Gadolinium-enhanced Magnetic Resonance Imaging Scans in Patients with Early, Relapsing-Remitting Multiple Sclerosis: Implications for Clinical Trials and Natural History," *Ann. Neurol.* 29:548-555, American Neurological Association, United States (1991).

Hartung, H.-P., et al., "The Role of Macrophages and Eicosanoids in the Pathogenesis of Experimental Allergic Neuritis," *Brain* 111:1039-1059, Oxford University Press, England (1988).

Hemminki, A., et al., "In Vivo Molecular Chemotherapy and Noninvasive Imaging With an Infectivity-Enhanced Adenovirus," *J. Natl. Cancer Inst.* 94(10):741-749, Oxford University Press, United States (2002).

Ji, H., et al., "Different modes of pathogenesis in T-cell-dependent autoimmunity: clues from two TCR transgenic systems," *Immunol. Rev.* 169:139-146, Munksgaard International Publishers, Denmark (1999).

Kappos, L., et al., "Efficacy of a novel oral single-agent Fumarate, BG00012, in patients with relapsing-remitting multiple sclerosis: results of a phase II study," oral presentation on May 30, 2006, at the 16th Meeting of the European Neurological Society, May 27-31, 2006, Lausanne, Switzerland.

Kappos, L., et al., "Efficacy of a novel oral single-agent fumarate, BG00012, in patients with relapsing-remitting multiple sclerosis: results of a phase 2 study," Abstract O108, Proceedings of the 16th Meeting of the European Neurological Society, May 27-31, 2006, Lausanne, Switzerland (Abstract Only).

Kappos, L., et al., "The Efficacy of BG00012 in Patients With Relapsing-Remitting Multiple Sclerosis: Subgroup Analyses From the Phase 2b Study," poster from the 60th Annual Meeting of the American Academy of Neurology, Apr. 12-19, 2008, Chicaro, IL, United States.

Kermode, A.G., et al., "Breakdown of the Blood-Brain Barrier Precedes Symptoms and Other MRI Signs of New Lesions in Multiple Sclerosis," *Brain* 113:1477-1489, Oxford University Press, England (1990).

Kuroda, K. and Akao, M., "Antitumor and Anti-Intoxication Activities of Fumaric Acid in Cultured Cells," *Gann.* 72(5):777-782, Japanese Cancer Association and the Japanese Foundation for Cancer Research, Japan (1981).

Biosis Database, Accession No. PREV197662032843, English language abstract for Kuroda, K., et al., "Inhibitory Effect of Capsella-Bursa-Pastoris Extract on Growth of Ehrlich Solid Tumor in Mice," *Cancer Res.* 36(6):1900-1903, American Association for Cancer Research, United States (1976) (Abstract Only).

Linker, R.A., et al., "CNTF is a major protective factor in demyelinating CNS disease: A neurotrophic cytokine as modulator in neuroinflammation," *Nature Medicine* 8(6):620-624, Nature America Inc., United States (2002).

Lodie, T.A., et al., "Systematic Analysis of Reportedly Distinct Populations of Multipotent Bone Marrow-Derived Stem Cells Reveals a Lack of Distinction," *Tissue Eng.* 8(5):739-751, Mary Ann Liebert, Inc., United States (2002).

Mendel, I., et al., "A myelin oligodendrocyte glycoprotein peptide induces typical chronic experimental autoimmune encephalomyelitis in H-2$^b$ mice: fine specificity and T cell receptor Vβ expression of encephalitogenic T cells," *Eur. J. Immunol.* 25:1951-1959, VCH mbH, Germany (1995).

*The Merck Manual of Diagnosis and Therapy*, 15$^{th}$ Edition, Berkow, R. and Fletcher, A.J., eds., p. 327, Merck Sharp & Dohme Research Lab, United States (1987).

Nieboer, C., et al., "Treatment of psoriasis with fumarc acid derivates," *Proceedings of the 239th Meeting of the Netherlands Society for Dermatology and Venereology Amsterdam*, Feb. 14, 1987, Br. J. Dermatol. 117(6):791-92, Blackwell Scientific Publications, England (1987) (Abstract Only).

Nioi, P. and Hayes, J.D., "Contribution of NAD(P)H:quinone oxidoreductase 1 to protection against carcinogenesis, and regulation of its gene by the Nrf2 basic-region leucine zipper and the arylhydrocarbon receptor basic helix-loop-helix transcription factors," *Mutat. Res.* 555:149-171, Elsevier B.V Netherlands (2004).

Olsson, T., "15: Future prospects of cytokines in the pathogenesis and management of multiple sclerosis," in Frontiers in Multiple Sclerosis, vol. 2, p. 139-150, Siva, A., et al., eds., Martin Dunitz Ltd., England (1999).

Olsson, T., "Chapter 6: Cytokines in Multiple Sclerosis and Its Experimental Models," in *Neuroscience Intelligence Unit 5: T-Cell Autoimmunity and Multiple Sclerosis*, Londei, M., ed., p. 91-112, R.G. Landes Company, United States (1999).

Biosis Database, Accession No. PREV199497368291, English language abstract for Pearl, J.M., et al., "Fumarate-enriched blood cardioplegia results in complete functional recovery of immature myocardium," *Ann. Thorac. Surg.* 57(6):1636-1641, Elsevier, Netherlands (1994) (Abstract Only).

Peeters, A.J., et al., "Fumaric Acid Therapy for Psoriatic Arthritis. A Randomized, Double-blind, Placebo-controlled Study," *Br. J Rheumatol.* XXXI(7):502-504, British Association for Rheumatology and Rehabilitation, England (1992).

Peeters, A.J., et al., "Gunstig effect van fumaarzuurtherapie bij arthritis psoriatica: een dubbelblind, placebo-gecontroleerd onderzoek," *Ned. Tijdschr. Geneeskd.* 136(49):2428-2431, Bohn Stafleu van Loghum, Netherlands (1992) (Abstract Only in English).

Perrella, O., et al., "Interleukin-10 and IFN-α in multiple sclerosis: is there a balance?" *J. Neurovirol.* 3(Suppl 1):P17, Stockton Press, United States (1997) (Abstract Only).

Polman, C.H., et al., "Diagnostic Criteria for Multiple Sclerosis: 2005 Revisions to the McDonald Criteria," *Ann. Neurol.* 58(6):840-846, Wiley-Liss, Inc., United States (2005).

Prochaska, H.J. and Santamaria, A.B., "Direct Measurement of NAD(P)H:Quinone Reductase from Cells Cultured in Microtiter Wells: A Screening Assay for Anticarcinogenic Enzyme Inducers," *Anal. Biochem.* 169:328-336, Academic Press, Inc., United States (1988).

Roitt, I.M., et al., eds., "23.Autoimmunity and Autoimmune Disease," in *Immunology*, p. 23.1-23.12, Gower Medical Publishing, United States (1985).

Rostami-Yazdi, M., et al., "Detection of Metabolites of Fumaric Acid Esters in Human Urine: Implications for Their Mode of Action," *J. Invest. Dermatol.* 129:231-234, Nature Publishing Group, United States (2008).

Rushmore, T.H., et al., "The Antioxidant Responsive Element: Activation by Oxidative Stress and Identification of the DNA Consensus Sequence Required for Functional Activity," *J. Biol. Chem.* 266(18):11632-11639, The American Society for Biochemist.), and Molecular Biology, Inc., United States (1991).

Biosis Database, Accession No. PREV199699044855, English language abstract for Schmidt, K.N, et al., "Anti-psoriatic drug anthralin activates transcription factor NF-kappa-B in murine keratinocytes," *J. Immunol.* 156(11):4514-4519, American Association of Immunologists, United States (1996) (Abstract Only).

Shi, N., et al., "Brain-specific expression of an exogenous gene after i.v. administration," *Proc. Natl. Acad. Sci. USA* 98(22):12754-12759, National Academy of Sciences, United States (2001).

Sobel, R.A., et al. "The Immunopathology of Experimental Allergic Encephalomyelitis. I. Quantitative Analysis of Inflammatory Cells In Situ," *J. Immunol.* 132(5):2393-2401, American Association of Immunologists, United States (1984).

Stangel, M., et al., "Fumarat in der Behandlung der Multiplen Sklerose: Mögliche Wirkmechanismen und Studien," *Der Nervenarzt* 79:212-217, Springer Medizin Verlag, Germany (2008) (Abstract Only in English).

Stühlinger, W., et al., "Nephrotoxische Wirkung einer Therapie mit Fumarsäureestern bei Psoriasis," *Dtsch., Med. Wschr.* 115:1712-1715, Georg Thieme Verlag Stuttgart, Germany (1990) (Abstract Only in English).

Traugott, U., "Detailed Analysis of Early Immunopathologic Events during Lesion Formation in Acute Experimental Autoimmune Encephalomyelitis," *Cell. Immunol.* 119:114-129, Academic Press, Inc., United States (1989).

Tung, C.-H., et al., "In Vivo Imaging of Proteolytic Enzyme Activity Using a Novel Molecular Reporter," *Cancer Res. 60*:4953-4958, American Association for Cancer Research, Inc., United States (2000).

Tuohy, V.K., et al., "A Synthetic Peptide From Myelin Proteolipid Protein Induces Experimental Allergic Encephalomyelitis," *J. Immunol. 141*(14):1126-1130, The American Association of Immunologists, United States (1988).

Úner, A.H., et al., "Characteristics of Auto Anti-idiotypic Antibodies Reactive with Antibodies Expressing the Pathogenic Idiotype, $Id^{LN}F_1$, in the $(NZB \times SWR)F_1$ Model for Lupus Nephritis and its Parental Strains," *J. Autoimmun. 11*:233-240, Academic Press, England (1998).

Van Muiswinkel, F.L., et al., "Expression of NAD(P)H:quinone oxidoreductase in the normal and Parkinsonian substantia nigra," *Neurobiol. Aging 25*:1253-1262, Elsevier Inc., United States (2004).

Van Muiswinkel, F.L. and Kuiperij, H.B., "The Nrf2-ARE Signalling Pathway: Promising Drug Target to Combat Oxidative Stress in Neurodegenerative Disorders," *Curr. Drug Targets—CNS & Neurol. Disord. 4*:267-281, Bentham Science Publishers Ltd., Netherlands (2005).

Weinmann, I., et al., "Influence of Fumaric Acid Derivates on T Lymphocytes in the Murine Model of HSV-1 Keratitis," *Invest. Opthalmol. Vis. Sci. 41*(4):S146, Association for Research in Vision and Ophthalmology annual meeting. Fort Lauderdale, Florida, USA, Apr. 30-May 5, 2000, United States (Abstract Only).

*The Merck Index: An Encyclopedia of Chemicals, Drugs, and Biologicals*, $10^{th}$ Edition, p. 396, Windholz, M., et al., eds., Merck & Co., Inc., United States (1983).

Zamvil, S., et al., "T-cell clones specific for myelin basic protein induce chronic relapsing paralysis and demyelination" *Nature 317*:355-358, Nature Publishing Group, England (1985).

Zamvil, S.S. and Steinman, L., "The T Lymphocyte in Experimental Allergic Encephalomyelitis," *Ann. Rev. Immunol. 8*:579-621, Annual Reviews Inc., United States (1990).

Office Action mailed Apr. 26, 2000, in U.S. Appl. No. 09/194,862, Joshi, R.K., et al., § 371(c) date Jul. 8, 1999 (now U.S. Patent No. 6,436,992 B1).

Office Action mailed Oct. 31, 2000, in U.S. Appl. No. 09/402,103, Joshi, R.K., et al., § 371(c) date Sep. 27, 1999 (now U.S. Patent No. 6,277,882 B1).

Office Action mailed May 21, 2001, in U.S. Appl. No. 09/743,978, Joshi, R.K., et al., § 371(c) date Jan. 17, 2001 (now U.S. Pat. No. 6,355,676 B1).

Office Action mailed Dec. 7, 2001, in U.S. Appl. No. 09/831,620, Joshi, R.K., et al., § 371(c) date May 10, 2001 (now U.S. Pat. No. 6,509,376 B1).

Office Action mailed Mar. 4, 2002, in U.S. Appl. No. 09/831,620, Joshi, R.K., et al., § 371(c) date May 10, 2001 (now U.S. Patent No. 6,509,376 B1).

Office Action mailed Aug. 12, 2003, in U.S. Appl. No. 10/148,858, Joshi, R.K., et al., § 371(c) date May 28, 2002 (now U.S. Patent No. 6,858,750 B2).

Office Action mailed Mar. 23, 2004, in U.S. Appl. No. 10/148,858, Joshi, R.K., et al., § 371(c) date May 28, 2002 (now U.S. Patent No. 6,858,750 B2).

Office Action mailed Mar. 22, 2004, in U.S. Appl. No. 10/197,077, Joshi, R.K., et al., filed Jul. 17, 2002 (now U.S. Patent No. 7,320,999 B2).

Office Action mailed Nov. 28, 2005, in U.S. Appl. No. 10/197,077, Joshi, R.K., et al., filed Jul. 17, 2002 (now U.S. Patent No. 7,320,999 B2).

Office Action mailed Jun. 21, 2006, in U.S. Appl. No. 10/197,077, Joshi, R.K., et al., filed Jul. 17, 2002 (now U.S. Patent No. 7,320,999 B2).

Office Action mailed May 15, 2007, in U.S. Appl. No. 10/197,077, Joshi, R.K., et al., filed Jul. 17, 2002 (now U.S. Patent No. 7,320,999 B2).

Office Action mailed Dec. 3, 2007, in U.S. Appl. No. 11/765,563, Joshi, R.K., et al., filed Jun. 20, 2007 (now U.S. Patent No. 7,612,110 B2).

Office Action mailed Sep. 9, 2008, in U.S. Appl. No. 11/765,563, Joshi, R.K., et al., filed Jun. 20, 2007 (now U.S. Patent No. 7,612,110 B2).

Office Action mailed Mar. 12, 2009, in U.S. Appl. No. 11/765,563, Joshi, R.K., et al., filed Jun. 20, 2007 (now U.S. Patent No. 7,612,110 B2).

Office Action mailed Dec. 14, 2007, in U.S. Appl. No. 11/765,578, Joshi, R.K., et al., filed Jun. 20, 2007 (now U.S. Patent No. 7,619,001 B2).

Office Action mailed Jul. 25, 2008, in U.S. Appl. No. 11/765,578, Joshi, R.K., et al., filed Jun. 20, 2007 (now U.S. Patent No. 7,619,001 B2).

Office Action mailed Sep. 15, 2008, in U.S. Appl. No. 11/765,578, Joshi, R.K., et al., filed Jun. 20, 2007 (now U.S. Patent No. 7,619,001 B2).

Office Action mailed Mar. 30, 2009, in U.S. Appl. No. 11/765,578, Joshi, R.K., et al., filed Jun. 20, 2007 (now U.S. Patent No. 7,619,001 B2).

Office Action mailed Oct. 2, 2009, in U.S. Appl. No. 12/405,661, Joshi, R.K., et al., filed Mar. 17, 2009 (now U.S. Patent No. 7,803,840 B2).

Office Action notification date Jan. 19, 2010, in U.S. Appl. No. 12/405,661, Joshi, R.K., et al., filed Mar. 17, 2009 (now U.S. Patent No. 7,803,840 B2).

Office Action notification date May 20, 2010, in U.S. Appl. No. 12/405,661, Joshi, R.K., et al., filed Mar. 17, 2009 (now U.S. Patent No. 7,803,840 B2).

Office Action notification date Mar. 23, 2010, in U.S. Appl. No. 12/405,665, Joshi, R.K., et al., filed Mar. 17, 2009 (now U.S. Patent No. 7,915,310 B2).

Office Action notification date Sep. 9, 2010, in U.S. Appl. No. 12/405,665, Joshi, R.K., et al., filed Mar. 17, 2009 (now U.S. Patent No. 7,915,310 B2).

Wallace, D.C., "Mitochondrial Diseases in Man and Mouse," *Science 283*:1482-1488, American Association for the Advancement of Science, United States (1999).

Schimrigk, et al., "Oral fumaric acid esters for the treatment of active multiple sclerosis: an open-label, baseline-controlled pilot study", European Journal of Neurology, vol. 13, No. 6, XP-002496537, pp. 604-610, (Jun. 2006).

Wierinckx, et al., "Detoxication enzyme Inducers modify cytokine production in rat mixed glial cells", Journal of Neuroimmunology, Elsevier Science Publishers BV, XX, vol. 166, No. 1-2, XP-005000427, pp. 132-143 (Sep. 1, 2005).

Memorandum of Meeting Minutes for the meeting held on Aug. 30, 2006, between attendees from the FDA and Biogen Idec regarding the End of Phase 2 for application PIND 73,061, BG00012.

Altmeyer, P. and Nüchel, C., "Systemtherapie der Psoriasis," *Dtsch. med. Wschr. 121*:1605-1607, Georg Thieme Verlag, Germany (1996).

English language translation of Altmeyer, P. and Nüchel, C., "Systemtherapie der Psoriasis," *Dtsch. med. Wschr. 121*:1605-1607, Georg Thieme Verlag, Germany (1996).

Altmeyer, P. and Nüchel, C., "Systemische Therapie der Psoriasis," *T&E Dermatologie 27*:380-382, 384, Reed Elsevier Deutschland, Germany (1997).

English language translation of Altmeyer, P. and Nüchel, C., "Systemische Therapie der Psoriasis," *T&E Dermatologie 27*:380-382, 384, Reed Elsevier Deutschland, Germany (1997).

Compston, A., et al., "The person with multiple sclerosis: a prospectus," in *McAlpine's Multiple Sclerosis, 4th Edition*, p. 803-810, Compston, A., et al., eds., Elsevier Inc., China (2006).

Kraft, A.D., et al., "Nuclear Factor E2-Related Factor 2-Dependent Antioxidant, Response Element Activation by tert-Butylhydroquinone and Sulforaphane Occurring Preferentially in Astrocytes Conditions Neurons against Oxidative Insult," *J. Neurosci. 24*(5):1101-1112, Society for Neuroscience, United States (2004).

Malipiero, U., et al., "Myelin oligodendrocyte glycoprotein-induced autoimmune encephalomyelitis is chronic/relapsing in perforin knockout mice, but monophasic in Fas- and Fas ligand-deficient *lpr* and *gld* mice," *Eur. J. Immunol. 27*(12):3151-3160, Wiley-VCH Verlag GmbH, Germany (1997).

McDonald, W.I., et al., "Recommended Diagnostic Criteria for Multiple Sclerosis: Guidelines from the International Panel on the Diagnosis of Multiple Sclerosis," *Ann. Neurol.* 50(1):121-127, Wiley-Liss, Inc., United States (2001).

Misgeld, T., "Death of an axon: studying axon loss in development and disease," *Histochem. Cell Biol.* 124:189-196, Springer-Verlag, Germany (2005).

Mrowietz, U., "Nephrotoxische Wirkung durch Fumarsäure," *Der Hautarzt* 51:615, Springer-Verlag, Germany (2000).

English language translation of Mrowietz, U., "Nephrotoxische Wirkung durch Fumarsäure," *Der Hautarzt* 51:615, Springer-Verlag, Germany (2000).

Noseworthy, J., et al., "The treatment of symptoms in multiple sclerosis and the role of rehabilitation," in *McAlpine's Multiple Sclerosis, 4th Edition*, p. 701-728, Compston, A., et al., eds., Elsevier Inc., China (2006).

Noseworthy, J., et al., "Disease-modifying treatments in multiple sclerosis," in *McAlpine's Multiple Sclerosis, 4th Edition*, p. 729-802, Compston, A., et al., eds., Elsevier Inc., China (2006).

Riemekasten, G., et al., "Strong Acceleration of Murine Lupus by Injection of the $SmD1^{83-119}$ Peptide," *Arthritis & Rheum.* 44(11):2435-2445, Wiley-Liss, Inc., United States (2001).

Sadjak, A., et al., "Nephrotoxische Wirkung von Fumarsäurederivaten," *Dtsch. med. Wschr.* 116(12):478, Georg Thiem Verlag, Germany (1991).

English language translation of Sadjak, A., et al., "Nephrotoxische Wirkung von Fumarsäurederivaten," *Dtsch. med. Wschr.* 116(12):478, Georg Thieme Verlag, Germany (1991).

English language translation of Germany Patent Publication No. DE 25 30 372 A1.

English language translation of Germany Patent Publication No. DE 26 21 214 A1.

English language translation of Germany Patent Publication No. DE 28 40 498 B1.

Balasubramaniam, P., et al., "Fumaric acid esters in severe psoriasis, including experience of use in combination with other systemic modalities," *Br. J. Dermatol.* 150:741-746, British Association of Dermatologists, England (2004).

Ffrench-Constant, C., "Pathogenesis of multiple sclerosis," *Lancet* 343(8892):271-275, The Lancet Ltd., England (1994).

Ghoreschi, K., et al., "A molecule solves psoriasis? Systemic therapies for psoriasis inducing interleukin 4 and Th2 responses," *J. Mol. Med.* (Berl.) 81(8):471-480, Springer-Verlag, Germany (2003).

Hartung, H.-P., et al., "Circulating adhesion molecules and inflammatory mediators in demyelination: A review," *Neurology* 45(6)(Suppl. 6):S22-S32, Advanstar Communications Inc., United States (1995).

Lee, J.-M., et al., "Nrf2, a multi-organ protector?" *FASEB J.* 19(9):1061-1066, Federation of American Societies for Experimental Biology, United States (2005).

Loewe, R., et al., "Dimethylfumarate Inhibits Tumor-Necrosis-Factor-Induced CD62E Expression in an NF-κb-Dependent Manner," *J. Invest. Dermatol.* 117:1363-1368, The Society for Investigative Dermatology, United States (2001).

Sormani, M.P., et al., "Clinical trials of multiple sclerosis monitored with enhanced MRI: new sample size calculations based on large data sets," *J. Neurol. Neurosurg. Psychiatry* 70:494-499, British Medical Association, England (2001).

Traugott, U., et al., "Multiple Sclerosis Distribution of T Cells, T Cell Subsets and Ia-positive Macrophages in Lesions of Different Ages," *J. Neuroimmunol.* 4:201-221, Elsevier Science Publishers, Netherlands (1983).

Traugott, U. and Lebon, P., "Multiple Sclerosis: Involvement of Interferons in Lesion Pathogenesis," *Ann. Neurol.* 24(2):243-251, American Neurological Association, United States (1988).

Walsh, M.J. and Tourtellotte, W.W., "Temporal Invariance and Clonal Uniformity of Brain and Cerebrospinal IgG, IgA, and IgM in Multiple Sclerosis," *J. Exp. Med.* 163:41-53, Rockefeller University Press, United States (1986).

"BG 12 BG 00012, BG 12/Oral Fumarate, FAG-201, Second-Generation Fumarate Derivative—Fumapharm/Biogen Idec," *Drugs in R&D* 6(4):229-230, Adis Data Information BV, New Zealand (2005).

"Efficacy and Safety of BG00012 in MS," ClinicalTrials.gov, accessed at http://www.clinicaltrials.gov/ct2/show/NCT00168701?term-bg00012&rank=3, accessed on Sep. 19, 2008, 3 pages.

"Efficacy and Safety of Oral BG00012 in Relapsing-Remitting Multiple Sclerosis (Define)," ClinicalTrials.gov, accessed at http://www.clinicaltrials.gov/ct2/show/NCT00420212?term=bg00012&rank=1, accessed on Sep. 19, 2008, 4 pages.

"Biogen Idec Announces Positive Top-Line Results from Second Phase 3 Trial Investigating Oral BG-12 (Dimethyl Fumarate) in Multiple Sclerosis," accessed at http://www.biogenidec.com/PRESS_RELEASE_DETAILS.aspx?ID-5981&ReqId=1621631, accessed on Oct. 28, 2011, 3 pages.

Langner, A., et al., "Results of a Phase II Study of a Novel Oral Fumarate, BG00012, in the Treatment of Severe Psoriasis," European Congress on Psoriasis, Oct. 21-24, 2004, Paris, France.

Langner, A., et al, "The Efficacy and Safety of a Novel Oral Formulation of Dimethylfumarate, BG00012, in Patients with Severe Psoriasis: Results of a Phase 2 Dose-Finding and Safety Extension Study," 3rd Spring Symposium of the European Academy of Dermatolo and Venerology (EADV), 2005, Sofia, Bulgaria.

Langner, A., et al., "Oral Fumarate for the Treatment of Severe Forms of Psoriasis: Results of a Phase II Clinical Study," $2^{nd}$ Spring Symposium of the European Academy of Dermatology and Venerology (EADV) Apr. 29-May 1, 2004, Budapest, Hungary.

Langner, A., et al., "Effects of a Novel Oral Fumarate, BG00012, in Patients with Severe Psoriasis: Results of a Phase 2 Study," $13^{th}$ Congress of the European Academy of Dermatology and Venerology (EADV), Nov. 17-21, 2004, Florence, Italy.

Langner, A., et al., "Efficacy and Safety of a New Oral Formulation of Fumaric Acid Ester for the Treatment of Moderate to Severe Psoriasis," $10^{th}$ International Psoriasis Symposium, Jun. 10-13, 2004, Toronto, Canada.

T Hart et al., "Modelling of multiple sclerosis: lessons learned in a non-human primate," *The Lancet Neurology* 3(10):588-597, Elsevier Ltd. (2004).

Office Action mailed Jul. 13, 2011, in U.S. Appl. No. 12/526,296, Lukashev et al., § 371(c) Date: Jan. 13, 2011.

Office Action mailed Dec. 15, 2011, in U.S. Appl. No. 12/526,296, Lukashev et al., § 371(c) Date: Jan. 13, 2011.

"Efficacy and Safety Study of Oral BG00012 with Active Reference in Relapsing-Remitting Multiple Sclerosis (Confirm)," ClinicalTrials.gov, accessed at http://www.clinicaltrials.gov/ct2/show/NCT00451451?term=bg00012&rank=8, 4 pages.

Office Action mailed Mar. 20, 2012, in U.S. Appl. No. 12/525,805, Gold, § 371(c) Date: Feb. 1, 2010.

International Search Report for International Patent Application No. PCT/US10/01282, International Searching Authority, United States, mailed on Jun. 28, 2010.

International Preliminary Report on Patentability for International Patent Application No. PCT/US10/01282, International Bureau of WIPO, Switzerland, issued Nov. 1, 2011.

Lee, D.-H., et al. "Spotlight on fumarates," *Int. MS J.* 15(1):12-18, Cambridge Medical Publications, England (2008).

Co-pending U.S. Appl. No. 13/465,740, inventor Lukashev, filed May 7, 2012.

European Patent Office Communication dated Oct. 30, 2012 in European Patent Application No. EP 08725256.5 regarding observations by a third party.

SEQUENCE LISTING

```
<160> NUMBER OF SEQ ID NOS: 18

<210> SEQ ID NO 1
<211> LENGTH: 9
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic core nucleotide sequence"
<220> FEATURE:
<221> NAME/KEY: modified_base
<222> LOCATION: (5)..(7)
<223> OTHER INFORMATION: a, c, g, t, unknown or other

<400> SEQUENCE: 1 tgabnnngc                                                              9

<210> SEQ ID NO 2
<211> LENGTH: 9
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic core nucleotide sequence"
<220> FEATURE:
<221> NAME/KEY: modified_base
<222> LOCATION: (5)..(7)
<223> OTHER INFORMATION: a, c, g, t, unknown or other

<400> SEQUENCE: 2 tgabnnngc                                                              9

<210> SEQ ID NO 3
<211> LENGTH: 11
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic core nucleotide sequence"
<220> FEATURE:
<221> NAME/KEY: modified_base
<222> LOCATION: (6)..(8)
<223> OTHER INFORMATION: a, c, g, t, unknown or other

<400> SEQUENCE: 3
rtgabnnngc r                                                          11
```

```
<210> SEQ ID NO 4
<211> LENGTH: 11
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic oligonucleotide"
<220> FEATURE:
<221> NAME/KEY: modified_base
<222> LOCATION: (5)..(8)
<223> OTHER INFORMATION: a, c, g, t, unknown or other

<400> SEQUENCE: 4
gtgannnngc a                                                              11

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 5
agtcacagtg agtcggcaaa attt                                                24

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 6
agtcacagtg acttggcaaa atct                                                24

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 7
agtcacagtg actcagcaga atct                                                24

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 8
gctaatggtg acaaagcaac tttc                                                24

<210> SEQ ID NO 9
<211> LENGTH: 24
<212> TYPE: DNA
<213> ORGANISM: Artificial Sequence
```

```
<220> FEATURE:
<221> NAME/KEY: source
<223> OTHER INFORMATION: /="Description of Artificial Sequence:
      Synthetic construct"

<400> SEQUENCE: 9
gctaatggtg acaaagcaac tttc                                              24

<210> SEQ ID NO 10
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 10
ctcaggcatg acattgcatt tttc                                              24

<210> SEQ ID NO 11
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 11
agtcactatg attcagcaac aaaa                                              24

<210> SEQ ID NO 12
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 12
cctccccgtg actcagcgct ttgt                                              24

<210> SEQ ID NO 13
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 13
gaagacaatg actaagcaga aatc                                              24

<210> SEQ ID NO 14
<211> LENGTH: 24
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"

<400> SEQUENCE: 14
cccaaccatg acacagcata aaag                                              24
```

```
<210> SEQ ID NO 15
<211> LENGTH: 9
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"
<220> FEATURE:
<221> NAME/KEY: modified_base
<222> LOCATION: (5)..(7)
<223> OTHER INFORMATION: a, c, g, t, unknown or other

<400> SEQUENCE: 15 tgacnnngc                                                                    9

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /="Description of Artificial Sequence:
      Synthetic construct"
<220> FEATURE:
<221> NAME/KEY: modified_base
<222> LOCATION: (4)..(5)
<223> OTHER INFORMATION: a, c, g, t, unknown or other
<220> FEATURE:
<221> NAME/KEY: modified_base
<222> LOCATION: (11)..(13)
<223> OTHER INFORMATION: a, c, g, t, unknown or other

<400> SEQUENCE: 16
taannatgac nnngcaaaaa                                                       20

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /="Description of Artificial Sequence:
      Synthetic oligonucleotide"

<400> SEQUENCE: 17
ucauugaacu gcucuuuggu u                                                     21

<210> SEQ ID NO 18
<211> LENGTH: 21
<212> TYPE: RNA
<213> ORGANISM: Artificial Sequence
<220> FEATURE:
<221> NAME/KEY: source
<223> OTHER INFORMATION: /="Description of Artificial Sequence:
      Synthetic oligonucleotide"

<400> SEQUENCE: 18
gaauuaaggc gguuuguccu u                                                     21
```

TREATMENT FOR MULTIPLE SCLEROSIS

CROSS REFERENCE TO RELATED APPLICATIONS

This application is a continuation of U.S. patent application Ser. No. 12/526,296, §371(c) Date Jan. 13, 2011, now abandoned, which is the U.S. National Phase of International Application No. PCT/US2008/001602, filed Feb. 7, 2008, which claims the benefit of U.S. Provisional Application 60/888,921, filed Feb. 8, 2007.

Provided are certain compounds for treating neurological diseases, including demyelinating neurological diseases, such as, e.g., multiple sclerosis.

Multiple sclerosis (MS) is an autoimmune disease with the autoimmune activity directed against central nervous system (CNS) antigens. The disease is characterized by inflammation in parts of the CNS, leading to the loss of the myelin sheathing around neuronal axons (demyelination), loss of axons, and the eventual death of neurons, oligodenrocytes and glial cells.

An estimated 2,500,000 people in the world suffer from MS. It is one of the most common diseases of the CNS in young adults. MS is a chronic, progressing, disabling disease, which generally strikes its victims some time after adolescence, with diagnosis generally made between 20 and 40 years of age, although onset may occur earlier. The disease is not directly hereditary, although genetic susceptibility plays a part in its development. Relapsing-remitting MS presents in the form of recurrent attacks of focal or multifocal neurologic dysfunction. Attacks may occur, remit, and recur, seemingly randomly over many years. Remission is often incomplete and as one attack follows another, a stepwise downward progression ensues with increasing permanent neurological deficit.

Although various immunotherapeutic drugs can provide relief in patients with MS, none is capable of reversing disease progression, and some can cause serious adverse effects. Most current therapies for MS are aimed at the reduction of inflammation and suppression or modulation of the immune system. As of 2006, the available treatments for MS reduce inflammation and the number of new episodes but not all have an effect on disease progression. A number of clinical trials have shown that the suppression of inflammation in chronic MS rarely significantly limits the accumulation of disability through sustained disease progression, suggesting that neuronal damage and inflammation are independent pathologies. Promoting CNS remyelination as a repair mechanism and otherwise preventing axonal loss and neuronal death are some of the important goals for the treatment of MS. For a comprehensive review of MS and its current therapies, see, e.g., McAlpine's Multiple Sclerosis, by Alastair Compston et al., 4th edition, Churchill Livingstone Elsevier, 2006.

"Phase 2 enzymes" serve as a protection mechanism in mammalian cells against oxygen/nitrogen species (ROS/RNS), electrophiles and xenobiotics. These enzymes are not normally expressed at their maximal levels and, their expression can be induced by a variety of natural and synthetic agents. Nuclear factor E2-related factor 2 (Nrf2) is a transcription factor responsible for the induction of a variety of important antioxidant and detoxification enzymes that coordinate a protective cellular response to metabolic and toxic stress.

ROS/RNS are most damaging in the brain and neuronal tissue, where they attack post-mitotic (i.e., non-dividing) cells such as glial cells, oligodendocytes, and neurons, which are particularly sensitive to free radicals. This process leads to neuronal damage. Oxidative stress has been implicated in the pathogenesis of a variety of neurodegenerative diseases, including ALS, Alzheimer's disease (AD), and Parkinson's disease (PD). For review, see, e.g., van Muiswinkel et al., Curr. Drug Targets CNS—Neurol. Disord., 2005, 4:267-281. An anti-oxidative enzyme under control of Nrf2, NQO1 (NAD(P)H dehydrogenase, quinone (1), was recently reported to be substantially upregulated in the brain tissues of AD and PD subjects (Muiswinkel et al., Neurobiol. Aging, 2004, 25: 1253). Similarly, increased expression of NQO1 was reported in the ALS subjects' spinal cord (Muiswinkel et al., Curr. Drug Targets—CNS. Neurol. Disord., 2005, 4:267-281) and in active and chronic lesions in the brains of patients suffering from MS (van Horssen et al., Free Radical Biol. & Med., 2006, 41 311-311). These observations indicate that the Nrf2 pathway may be activated in neurodegenerative and neuroinflammatory diseases as an endogenous protective mechanism. Indeed, most recently, it has been reported that induced activation of Nrf2-dependent genes by certain cyclopenanone-based compounds (NEPP) counters the toxic effects of metabolic inhibition and ROS/RNS production in the brain and protects neurons from death in vitro and in vivo (see Satoh et al., PNAS, 2006, 103(3):768-773).

Additionally, many publications have reported neuroprotective effects of compounds in natural plant-derived compounds ("phytochemicals"), including α-tocopherol (vitamin E), lycopene (tomatoes), resveratrol (red grapes), sulforaphane (broccoli), EGCG (green tea), etc. For review, see Mattson and Cheng, Trends in Neurosci., 2006, 29(11):632-639. Originally, the action of these compounds was attributed to their anti-oxidant properties. However, while most anti-oxidants are effective only at high concentrations, at least some of these compounds appear to exert neuroprotective effects at much lower doses. Emerging evidence suggests that these compounds may exert their neuroprotective effects by activating cellular stress-response pathways, including the Nrf2 pathway, resulting in the upregulation of neuroprotective genes. However, the exact mechanism of action of these compounds remains poorly understood.

To date, more than 10 different chemical classes of inducers of Nrf2 pathway have been identified including isothiocyanates and their thiol addition products, dithiocarbamates, as well as 1,2-dithiole-3-thiones, trivalent arsenic derivatives (e.g., phenyl arsenoxide), heavy metals, certain conjugated cyclic and acyclic polyenes (including porphyrins, chlorophyllins, and chlorophyll), and vicinal dimercaptans. These inducers have few structural similarities. They are mostly electrophiles, and all can react chemically with thiol groups by alkylation, oxidation, or reduction, suggesting that the intracellular sensor for inducers is likely to contain very highly reactive (cysteine) thiols. The inducers can modify thiol groups by a variety of mechanisms including: alkylation (Michael addition acceptors, isothiocyanates, quinones); oxidation (e.g., peroxides and hydroperoxides); and direct reaction with thiol/disulfide linkages (e.g., vicinal dithiols such as 1,2-dimercaptopropanol, lipoic acid). These diverse response mechanisms provide plasticity for cellular responses to a variety of electrophilic and oxidant stressors.

Provided are methods that comprise at least one of the following methods:
1) methods of screening for at least one new candidate compound for treating a neurological disease;
2) methods of evaluating neuroprotective properties of at least one drug candidate for treating a neurological disease;
3) methods of comparing (e.g., for bioequivalence) at least two pharmaceutical compositions which comprise fumaric acid derivatives;

4) methods of treating a neurological disease by administering to the subject in need thereof at least one compound that is partially structurally similar to DMF or MMF; and
5) methods of treating a neurological disease by a combination therapy that comprises administration of at least one first compound that upregulates the Nrf2 pathway and at least one second compound that does not upregulate the Nrf2 pathway.

In some embodiments, the neurological disease is a neurodegenerative disease such as, for example, ALS, Parkinson's disease, Alzheimer's disease, and Huntington's disease. In some embodiments the neurological disease is MS or another demyelinating neurological disease.

In some embodiments, the methods 1-3 further comprise:
a) contacting a cell with the test compound, and
b) determining whether the Nrf2 pathway is upregulated in the cell.

In some embodiments, the methods may further comprise:
c) determining whether the test compound slows or prevents demyelination, axonal loss, and/or neuronal death, and/or
d) selecting the test compound as a candidate for treating neurodegeneration in a neurological disease if 1) the Nrf2 pathway is upregulated and 2) demyelination, axonal loss, and/or neuronal death are/is prevented or slowed.

In some embodiments, the methods 1-3 comprise contacting a cell with at least one test compound and determining whether the Nrf2 pathway is upregulated in the cell. In such methods, an upregulation of the Nrf2 pathway above a threshold (e.g., by at least 30% over a control) indicates that the at least one compound has at least one biological property beneficial in treating a neurological disease (e.g., neuroprotective properties). In some embodiments, the upregulation of the Nrf2 pathway is assessed (in vivo and/or in vitro) by at least one of the following:
i) expression levels of endogenously produced and/or exogenously introduced Nrf2;
ii) subcellular localization and/or nuclear translocation of Nrf2;
iii) expression levels and/or activity of one or more genes under control of Nrf2 (e.g., endogenous NQO1) or an Nrf2-regulated reporter gene in an artificial reporter construct;
iv) levels of Nrf2 binding to the Nrf2-binding DNA element ARE;
v) stability of Nrf2/Keap1 complexes; and
vi) modification (e.g., alkylation) levels of Keap1 and/or at least one other Nrf2/Keap1-associated proteins.

In some embodiments of methods 1-3, the compounds that are being screened, evaluated, or compared comprise at least one member of at least one of the following classes of compounds: mild alkylating agents, Michael addition acceptors, and compounds that are metabolized upon administration to Michael addition acceptors. In some embodiments, the Michael addition acceptor has the structure of Formula I, II, III, or IV set forth below.

In some embodiments method 1 comprises:
a) contacting a cell with a plurality of test compounds,
b) determining whether the Nrf2 pathway is upregulated in the cell, and
c) selecting from the plurality of compounds at least one compound that upregulates the Nrf2 pathway,
wherein an upregulation of the Nrf2 pathway by the selected at least one compound indicates that the selected at least one compound may be useful for treating a neurological disease.

The plurality of compounds may be represented, e.g., by a combinatorial chemical library, and the method may be performed, e.g., by high-throughput screening.

In some embodiments method 2 comprises:
a) contacting a cell with the at least one drug or drug candidate, and
b) determining whether the Nrf2 pathway is upregulated in the cell,
wherein an upregulation of the Nrf2 pathway by the at least one drug or drug candidate indicates that the at least one drug or drug candidate is useful for neuroprotection in treating a human having a neurological disease.

In some embodiments method 3 comprises:
a) contacting a cell with a first composition comprising at least one test compound, and
b) comparing the level of Nrf2 pathway upregulation in the cell by the at least one test compound to the corresponding level of the Nrf2 pathway upregulation in a control cell treated with a second composition comprising at least one of DMF and MMF.

In some embodiments of method 3, the test compound is fumaric acid, a salt thereof, or a fumaric acid derivative. In some embodiments, the first composition comprises DMF, MMF, or both. In some embodiments, the dose and/or the formulation of the first composition differs from the dose and/or the formulation of the second composition.

In some embodiments, method 3 further comprises:
c) comparing at least one pharmacokinetic parameter (e.g., serum-half-life) of the first and the second compositions.

In some embodiments method 4 comprises administering to the mammal a therapeutically effective amount of at least one neuroprotective compound having Formula I, II, III, or IV, e.g., a fumaric acid derivative (e.g., DMF or MMF).

In some embodiments method 4 provides a method of slowing or preventing neurodegeneration in a patient in need thereof, by administering the compound in an amount and for a period of time sufficient to slow or prevent demyelination, axonal loss, and/or neuronal death, e.g., by at least 30% relative to a control.

In some embodiments method 5 comprises:
a) administering to the mammal a therapeutically effective amount of at least one first compound that upregulates the Nrf2 pathway, and
b) administering a therapeutically effective amount of at least one second compound that does not upregulate the Nrf2 pathway.

In some embodiments of method 5, the at least one first compound, used in step (a), is a compound of Formula I, II, III, or IV, e.g., a fumaric acid derivative (e.g., DMF or MMF); and the at least one second compound, which is used in step (b), is an immunosuppressive or an immunomodulatory compound that does not upregulate the Nrf2 pathway (e.g., by more than 30% over a control).

In some embodiments method 5 comprises administering to the mammal a therapeutically effective amount of a compound of Formula I, II, III, or IV.

In some embodiments of methods 1-5, the at least onecompound being screened, identified, evaluated, or used for treating a neurological disorder is not fumaric acid or its salt, or a fumaric acid derivative (e.g., DMF or MMF).

Other features and embodiments of the invention will be apparent from the following description and the claims.

Figure 1:
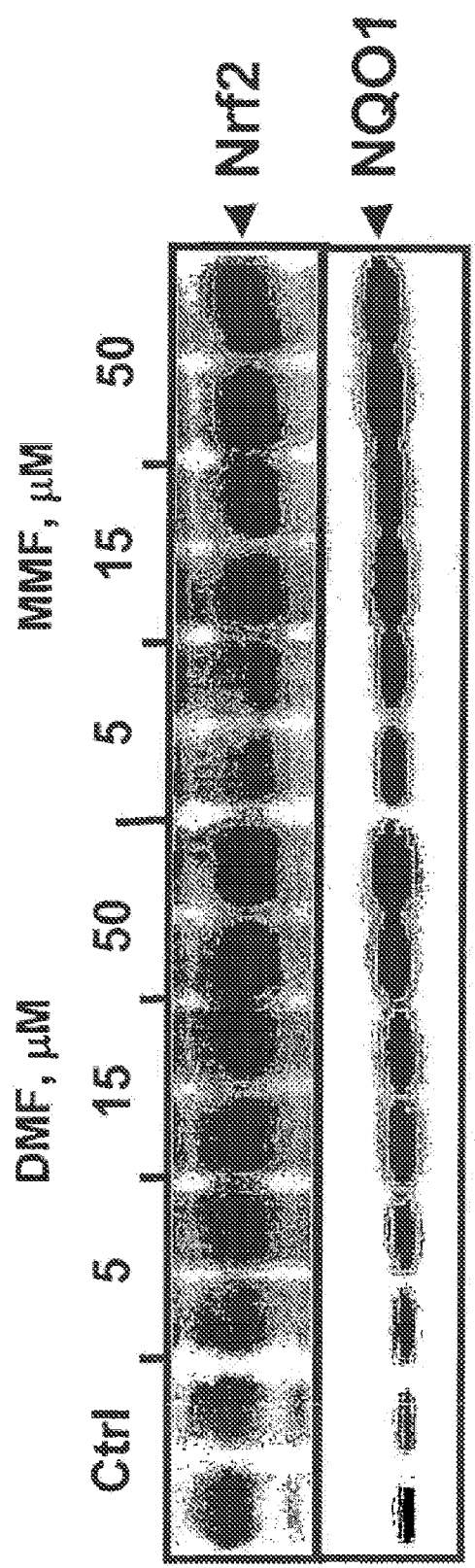
FIG. 1 demonstrates that DMF and MMF are activators of Nrf2 at concentrations within clinical exposure range (cells in culture).

Fumaric acid esters, such as DMF, have been proposed for treatment of MS (see, e.g., Schimrigk et al., Eur. J. Neurol., 2006, 13(6):604-10; Drugs R&D, 2005, 6(4):229-30).

Provided are, among other things, means for identifying compounds with a new therapeutic modality useful in at least one of multiple neurological indications and, optionally, complementary to other drugs for the treatment of a neurological disease, including a number of currently used immunomodulators.

DMF is a member of a large group of anti-oxidant molecules known for their cytoprotective and anti-inflammatory properties. These molecules also share the property of the Nrf2 pathway activation. Thus, the finding that DMF activates the Nrf2 pathway in conjunction with the neuroprotective effects of DMF further offers a rationale for identification of structurally and/or mechanistically related molecules that would be expected to be therapeutically effective for the treatment of neurological disorders, such as, e.g., MS.

Certain terms are defined in this section; additional definitions are provided throughout the description.

The terms "activation" and "upregulation," when used in reference to the Nrf2 pathway, are used interchangeably herein.

The terms "disease" and "disorder" are used interchangeably herein.

The term "a drug for treating a neurological disease" refers to a compound that has a therapeutic benefit in a specified neurological disease as shown in at least one animal model of a neurological disease or in human clinical trials for the treatment of a neurological disease.

The term "neuroprotection" and its cognates refer to prevention or a slowing in neuronal degeneration, including, for example, demyelination and/or axonal loss, and/or, neuronal and/or oligodendrocyte death. Neuroprotection may occur through several mechanisms, e.g., through reducing inflammation, providing neurotrophic factors, scavenging free radicals, etc. As used herein, a compound is considered neuroprotective if it (1) upregulates the Nrf2 pathway above a certain threshold and (2) provides neuroprotection, regardless of possible other mechanisms of action.

The terms "treatment," "therapeutic method," "therapeutic benefits," and the like refer to therapeutic as well as prophylactic/preventative measures. Thus, those in need of treatment may include individuals already having a specified disease and those who are at risk for acquiring that disease.

The terms "therapeutically effective dose" and "therapeutically effective amount" refer to that amount of a compound which results in at least one of prevention or delay of onset or amelioration of symptoms of a neurological disorder in a subject or an attainment of a desired biological outcome, such as reduced neurodegeneration (e.g., demyelination, axonal loss, and neuronal death) or reduced inflammation of the cells of the CNS.

In one aspect, provided are methods of evaluating neuroprotective properties of test compounds, including the following methods:

1) methods of screening for new candidate compounds that may be useful for treating a neurological disease;
2) methods of evaluating neuroprotective properties of drugs and candidates that are used or proposed for treating a neurological disease;
3) methods of comparing (e.g., for bioequivalence) two or more pharmaceutical compositions which contain fumaric acid derivatives;

In some embodiments, methods 1-3 may comprise:
a) contacting a cell with the test compound,
b) determining whether the Nrf2 pathway is upregulated in the cell, and, in some embodiments, additionally performing the following step(s):
c) determining whether the test compound slows or prevents demyelination, axonal loss, and/or neuronal death, and/or
d) selecting the test compound as a candidate for treating neurodegeneration in a neurological disease if 1) the Nrf2 pathway is upregulated and 2) demyelination, axonal loss, and/or neuronal death are/is prevented or slowed.

Method 1

In some embodiments the methods of screening for a candidate compound for treating a neurological disease comprise:
a) contacting a cell with a plurality of test compounds,
b) determining whether the Nrf2 pathway is upregulated in the cell, and
c) selecting from the plurality of compounds at least one compound that upregulates the Nrf2 pathway,
wherein an upregulation of the Nrf2 pathway by the selected at least one compound indicates that the selected at least one compound may be useful for treating a neurological disease. For example, the plurality of compounds may be represented by a combinatorial chemical library, and the screening method may be performed by a high-throughput screening as described in, e.g., High-Throughput Screening in Drug Discovery (Methods and Principles in Medicinal Chemistry), by Jörg Hüser (ed.), John Wiley & Sons (2006).

Combinatorial libraries of compounds are also described in, e.g., Solid-Supported Combinatorial and Parallel Synthesis of Small-Molecular-Weight Compound Libraries (Tetrahedron Organic Chemistry) Ian Salusbury (ed.), Elsevier (1998); Combinatorial Libraries: Synthesis, Screening and Application Potential (Library Binding), by Riccardo Cortese (ed.), Walter de Gruyter (1995). The libraries of compounds may be, for example, quinone libraries and other libraries as described in Mittoo, Comb. Chem. & High Throughput Screen, 2006, 9:421-423.

In some embodiments, the at least one compound or plurality of compounds being screened and/or selected comprises at least one compound selected from at least one of the following groups of compounds: mild alkylating agents, Michael addition acceptors or compounds that are metabolized to Michael addition acceptors, including compounds of Formulas I, II, III, or IV.

In some of the embodiments, the at least one compound is selected from fumaric acid, its salts, and fumaric acid derivatives.

Method 2

Also provided are methods of evaluating neuroprotective properties of at least one drug or drug candidate for treating at least one neurological disease. Such methods comprise:
a) contacting a cell with the at least one drug or drug candidate, and
b) determining whether the Nrf2 pathway is upregulated in the cell,
wherein the upregulation of the Nrf2 pathway by the at least one drug or drug candidate indicates that the at least one drug or drug candidate is neuroprotective in treating a human having a neurological disease.

In some embodiments, the upregulation of the Nrf2 pathway by the at least one drug or drug candidate indicates that the at least one drug or drug candidate has at least one activity selected from slowing demyelination, slowing the loss of axons, and slowing the rate of neuronal death.

In some embodiments, the method of evaluating at least one drug or drug candidate comprises an additional step:

c) evaluating demyelination, loss of axons, and/or neuronal death.

In some embodiments, steps a) and c) are performed in vivo in at least one model of a neurological disease, e.g., as described below.

In other embodiments, particularly those in which the neurological disease is multiple sclerosis or another demyelinating disease, the evaluated at least one drug or drug candidate for a neurological disease is chosen from the following: FTY720 (2-(4-octylphenethyl)-2-aminopropane-1,3-diol; Novartis); anti-IL12 antibody (e.g., ABT-874; Abbott Laboratories); GSK683699 (GSK/Tanabe); NeuroVax (Immune Response Corp.; Darlington, Curr. Opin. Mol. Ther., 2005, 7(6):598-603); anti-CCR2 antibody (e.g., MLN 1202; Millennium); interferon β-1a (e.g., Avonex®; Biogen Idec); anti-α4-integrin antibody (e.g., Tysabri®; Biogen Idec/Elan); anti-CD20 antibody (e.g., Rituxan® (Biogen Idec/Genentech); TV 5010 (Teva); NBI-788 (Neurocrine); MBP8298 (BioMS (see Warren et al., Eur. J. Neurol., 2006, 13(8):887-95); Mylinax (Oral Cladribine; 2-chlorodeoxyadenosine; Serono/IVAX); Teriflunomide ((Z)-2-cyano-N-(4-(trifluoromethyl)phenyl)-3-hydroxybut-2-enamide; Sanofi-Aventis); Temsirolimus (Wyeth); Laquinimod (5-chloro-N-ethyl-1,2-dihydro-4-hydroxy-1-methyl-2-oxo-N-phenylquinoline-3-carboxamide; Active Biotech/Teva); and interferon tau (Tauferon; Pepgen).

In some embodiments, the at least one drug or drug candidate being evaluated is at least one compound selected from at least one class selected from a mild alkylating agent, a Michael addition acceptor, and a compound that is metabolized to a Michael addition acceptor, including compounds of Formulas I, II, III, or IV.

In some of the embodiments, the compound is fumaric acid, its salt, or a fumaric acid derivative.

Method 3

Also provided are methods of comparing (e.g., for bioequivalence) at least two pharmaceutical compositions. Such methods comprise:

a) contacting a cell with at least one first composition comprising a test compound, and b) comparing the level of the Nrf2 pathway upregulation in the cell by the test compound to the corresponding level of the Nrf2 pathway upregulation in a cell treated with at least one second composition ("comparator composition") comprising DMF, MMF, or both.

In some embodiments, substantially dissimilar levels of upregulation by the at least one first and at least one second compositions indicate that the compositions are not bioequivalent.

In some embodiments, the test compound is fumaric acid, its salt thereof, a fumaric acid derivative, or mixtures thereof. In some embodiments, the first composition comprises at least one of DMF, MMF, and both DMF and MMF. In some embodiments, the dose and/or the formulation of the at least one first composition differs from the dose and/or the formulation of the at least one second composition. The at least one first composition may be a controlled release composition such as, e.g., compositions described in WO 2006/037342.

In some embodiments, the method further comprises and additional step:

c) comparing at least one pharmacokinetic parameter of the at least one first and the at least one second compositions.

Pharmacokinetic parameters and methods for evaluating the same are well known and are described in, e.g., Pharmacokinetics, Second Edition (Drugs and the Pharmaceutical Sciences) by Milo Gibaldi et al. (eds.), Informa Healthcare (1982). Examples of such pharmacokinetic parameters that can be evaluated include serum half-life, clearance, and volume distribution.

In some embodiments, substantially dissimilar pharmacokinetic parameter(s) of the a least one first and at least one second compositions indicate that the compositions are not bioequivalent.

In some embodiments, the test compound being evaluated is a mild alkylating agent, and more specifically, a Michael addition acceptor, or a compound that is metabolized to a Michael addition acceptor.

In some of the embodiments, the test compound is fumaric acid or its salt, or a fumaric acid derivative.

Also provided are methods of treating a mammal who has or is at risk for developing a neurological disease, including the following methods:

4) methods of treating a neurological disease by administering to the subject in need thereof at least one compound that is partially structurally similar to DMF or MMF (including compounds selected using methods 1-3 described above); and 5) methods of treating a neurological disorder by a combination therapy that includes administration of a first compound that does not upregulate the Nrf2 pathway and a second compound that upregulates the Nrf2 pathway.

Method 4

Also provided are methods of treating a neurological disease by administering to the subject in need thereof at least one compound that is at least partially structurally similar to DMF and/or MMF.

In some embodiments of method 4, a method of treating a mammal who has or is at risk for a neurological disease is provided. The methods comprises administering to the mammal a therapeutically effective amount of at least one neuroprotective compound which has Formula I, II, III, or IV, e.g., a fumaric acid derivative (e.g., DMF or MMF).

In some embodiments of method 4, a method of slowing or preventing neurodegeneration (more specifically, e.g., demyelination, axonal loss, and/or neuronal death) in a subject in need thereof, by administering the at least one compound in an amount and for a period of time sufficient to do at least one of slow or prevent demyelination, slow or prevent axonal loss, and slow or prevent neuronal death, e.g., by at least 30%, 50%, 100% or higher over a control over a period of at least 5, 10, 12, 20, 40, 52, 100, or 200 weeks, or more.

Method 5

Also provided are methods of treating a mammal having a neurological disease by combination therapy. In some embodiments such methods comprise:

a) administering to the mammal a therapeutically effective amount of at least one first compound that upregulates the Nrf2 pathway, and b) administering a therapeutically effective amount of at least one second compound that does not upregulate the Nrf2 pathway.

In some of embodiments of method 5, the at least one first compound, used in step (a), is a compound of Formula I, II, III, or IV, e.g., DMF or MMF; and the at least one second compound, which is used in step (b), is an immunosuppressive or an immunomodulatory compound that does not upregulate the Nrf2 pathway (e.g., by more than 30%, 50%, 100% over a control).

In some embodiments of method 5, the method comprises administering to the mammal a therapeutically effective amount of a compound of Formula I, II, III, or IV.

In method 5, the at least one first compound and the at least one second compound may be administered concurrently (as separate compositions or a mixed composition) or consecutively over overlapping or non-overlapping intervals. In the sequential administration, the at least one first compound and the at least one second compound can be administered in any order. In some embodiments, the length of an overlapping interval is more than 2, 4, 6, 12, 24, or 48 weeks, for example.

Michael addition acceptors generally include olefins or acetylenes conjugated to an electron withdrawing group, such as carbonyl containing groups, thiocarbonyl containing groups, cyano, sulfonyl, sulfonamido, amido, formyl, keto, and nitro. Exemplary carbonyl groups include carboxylic acid esters and carboxylic acid.

In some embodiments of methods 1-5, the at least one compound being screened, identified, evaluated, or used for treating a neurological disorder is selected from a mild alkylating agent, a Michael addition acceptor, and a compound that is metabolized to a Michael addition acceptor.

In some embodiments, the Michael addition acceptor has the structure of Formula I:

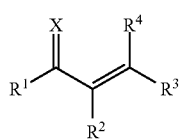

(I)

or a pharmaceutically acceptable salt thereof, wherein:
X is O; S; C(R)($C_{1-12}$)alkyl; or C(R)($C_{2-12}$)alkenyl, wherein R is H, ($C_{1-12}$)alkyl or ($C_{2-12}$)alkenyl;
$R^1$, $R^2$, $R^3$ and $R^4$ are independently selected from: H; OH; O$^-$; $CO_2H$, $CO_2^-$; SH; S$^-$; $SO_2H$, $SO_2^-$; ($C_{1-24}$)alkyl; ($C_{1-24}$)alkenyl; ($C_{6-50}$)aryl, $CO_2(C_{1-24}$)alkyl; $SO_2(C_{1-24}$)alkyl; $CO_2(C_{1-24}$)alkenyl; $SO_2(C_{1-24}$)alkenyl; $CO_2Y$, wherein Y is psoralen-9-yl, retinyl, alpha-tocopherol, calciferyl, corticostreoid-21-yl or monosaccarid-ω-yl; ($C_{1-24}$)alkoxy; ($C_{1-24}$)alkenyloxy; ($C_{6-50}$)aryloxy; ($C_{1-24}$)alkylthio; ($C_{1-24}$)alkenylthio; ($C_{6-50}$)arylthio, amino; amido; arylalkyl; cyano; nitro; sulfonyl; sulfoxido; sulfonamido; formyl; keto; and D and L natural or unnatural amino acids; or any two of X, $R^1$, $R^2$ and $R^3$, and $R^4$ may be joined together to form a cyclic moiety; and wherein the alkyl, alkoxy, alkenyl, alkenyloxy, aryl and aryloxy groups may be optionally substituted with at least one group chosen from halogen (F, Cl, Br, or I), OH, ($C_{1-4}$)alkoxy, nitro and cyano.

In some embodiments, the at least one Michael addition acceptor has the structure of Formula I, with the following provisos:
$R^1$ is selected from: H; OH; O$^-$; $CO_2H$, $CO_2$; SH; S$^-$; $SO_2H$, $SO_2^-$; ($C_{1-24}$)alkyl; ($C_{1-24}$)alkenyl; ($C_{6-50}$)aryl; $CO_2(C_{1-24}$)alkyl; $SO_2(C_{1-24}$)alkyl; $CO_2(C_{1-24}$)alkenyl; $SO_2(C_{1-24}$)alkenyl; $CO_2Y$, wherein Y is psoralen-9-yl, retinyl, alpha-tocopherol, calciferyl, corticostreoid-21-yl or monosaccarid-ω-yl; ($C_{1-24}$)alkoxy; ($C_{1-24}$)alkenyloxy; ($C_{6-50}$)aryloxy; ($C_{1-24}$)alkylthio; ($C_{1-24}$)alkenylthio; ($C_{6-50}$)arylthio; arylalkyl; amino; amido; cyano; nitro; sulfonyl, sulfoxido; sulfonamido; formyl, keto; and D or L natural or unnatural amino acids; and wherein the alkyl, alkoxy, alkenyl, alkenyloxy, aryl and aryloxy groups may be optionally substituted with at least one group chosen from halogen (F, Cl, Br, or I), OH, ($C_{1-4}$)alkoxy, nitro and cyano;
$R^2$ is selected from: H; $CO_2H$; $CO_2^-$; $SO_2H$; $SO_2^-$; ($C_{1-24}$)alkyl; ($C_{1-24}$)alkenyl; ($C_{6-50}$)aryl; $CO_2(C_{1-24}$)alkyl; $SO_2(C_{1-24}$)alkyl; $CO_2(C_{1-24}$)alkenyl; $SO_2(C_{1-24}$)alkenyl; $CO_2Y$, wherein Y is psoralen-9-yl, retinyl, alpha-tocopherol, calciferyl, corticostreoid-21-yl or monosaccarid-ω-yl; ($C_{1-24}$)alkoxy; ($C_{1-24}$)alkenyloxy; ($C_{6-50}$)aryloxy; ($C_{1-24}$)alkylthio; ($C_{1-24}$)alkenylthio; ($C_{6-50}$)arylthio, amido; arylalkyl; cyano; nitro; sulfonyl, sulfoxido, sulfonamido; formyl, keto; and D or L natural or unnatural amino acids; wherein the alkyl, alkoxy, alkenyl, alkyenyloxy, aryl and aryloxy groups may be optionally substituted with at least one group chosen from halogen (F, Cl, Br, or I), OH, ($C_{1-4}$)alkoxy, nitro and cyano; and
$R^3$ and $R^4$ are independently selected from: H; $CO_2H$; $CO_2^-$; $SO_2H$; $SO_2^-$; ($C_{1-24}$)alkyl; ($C_{1-24}$)alkenyl; ($C_{6-50}$)aryl; $CO_2(C_{1-24}$)alkyl; $SO_2(C_{1-24}$)alkyl; $CO_2(C_{1-24}$)alkenyl; $SO_2(C_{1-24}$)alkenyl; $CO_2Y$, wherein Y is psoralen-9-yl, retinyl, alpha-tocopherol, calciferyl, corticostreoid-21-yl or monosaccarid-ω-yl; ($C_{1-24}$)alkoxy; ($C_{1-24}$)alkenyloxy; ($C_{6-50}$)aryloxy; ($C_{1-24}$)alkylthio; ($C_{1-24}$)alkenylthio; ($C_{6-50}$)arylthio; amido; arylalkyl; cyano; nitro; cyano; nitro; sulfonyl; sulfoxido; sulfonamido; formyl; and keto; wherein the alkyl, alkoxy, alkenyl, alkyenyloxy, aryl and aryloxy groups may be optionally substituted with at least one group chosen from halogen (F, Cl, Br, or I), OH, ($C_{1-4}$)alkoxy, nitro and cyano.

In some embodiments, the at least one Michael addition acceptor has the structure of Formula II:

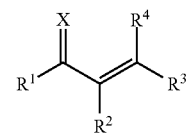

(II)

or a pharmaceutically acceptable salt thereof, wherein:
X is selected from O; S; C(R)($C_{1-12}$)alkyl; and C(R)($C_{2-12}$)alkenyl, wherein R is selected from H; ($C_{1-12}$)alkyl; and ($C_{2-12}$)alkenyl; and $R^1$, $R^2$, $R^3$, and $R^4$ are independently selected from: H; OH; O$^-$; $CO_2H$; $CO_2^-$; ($C_{1-12}$)alkyl; ($C_{1-12}$)alkenyl; and $CO_2(C_{1-12}$)alkyl;
or any two of X, $R^1$, $R^2$ and $R^3$ may be joined together to form a cyclic moiety.

In some embodiments of the compounds of Formulae I-IV, the pharmaceutically acceptable salt is a salt of a metal (M) cation, wherein M can be an alkali, alkaline earth, or transition metal such as Li, Na, K, Ca, Zn, Sr, Mg, Fe, or Mn.

In some embodiments of methods 1-5, the compounds of Formula I include fumaric acid, its salts, and fumaric acid derivatives.

In some embodiments, the at least one compound of Formula I has the structure of Formula III:

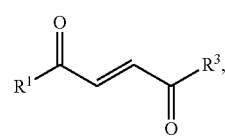

(III)

or a pharmaceutically acceptable salt thereof, wherein:
$R^1$ and $R^3$ are independently selected from OH; O$^-$; ($C_{1-24}$)alkoxy; ($C_{1-24}$)alkenyloxy; ($C_{6-50}$)aryloxy; psoralen-9-yloxy; retinyloxy; alpha-tocopheroloxy; calciferyloxy; corticostreoid-21-yloxy; monosaccarid-ω-yloxy; amino; and a D or L natural or unnatural amino acid; and wherein at least one of the $(C_{1-24})$alkoxy; $(C_{1-24})$alkenyloxy; and $(C_{6-50})$aryloxy groups may be optionally substituted with at least one group chosen from halogen (F, Cl, Br, or I), OH, $(C_{1-4})$alkoxy, nitro and cyano.

Compounds wherein at least one of $R^1$ and $R^3$ is derived from a natural or unnatural D or L amino acid are described in U.S. application Ser. Nos. 10/433,295, paragraphs 10 to 11 and 18-28, and 11/421,083, which are incorporated herein by reference.

In some embodiments, the compound of formula (I) has the structure of Formula IV:

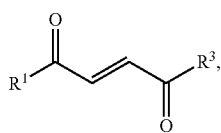

(IV)

or a pharmaceutically acceptable salt thereof, wherein:

$R^1$ and $R^3$ are independently selected from OH; O$^-$; $(C_{1-24})$alkoxy; allyloxy; vinyloxy; $(C_{6-50})$aryloxy; psoralen-9-yloxy; retinyloxy; alpha-tocopheroloxy; calciferyloxy; corticosteroid-21-yloxy; monosaccarid-ω-yloxy; amino; and a D or L natural or unnatural amino acid; and wherein at least one of the $(C_{1-24})$alkoxy, allyloxy, vinyloxy, and $(C_{6-50})$aryloxy may be optionally substituted with at least one group chosen from Cl, F, I, Br, OH, $(C_{1-4})$alkoxy, nitro, and cyano.

In some embodiments, the "fumaric acid derivative" is chosen from the compounds of Formula III, compounds of Formula IV and the following:

1) fumaric acid amides derived from natural and unnatural amino D or L acids, as described in U.S. patent application Ser. Nos. 10/433,295, paragraphs 10 to 11 and 18-28, and 11/421,083.

2) a carbocyclic or oxacyclic fumaric acid oligomer as described in U.S. patent application Ser. No. 10/511,564, paragraphs 15-44; and 3) a glycerol or alkane diol or polyol derivative of fumaric acid as described in U.S. Pat. Nos. 4,851,439, 5,149,695, 5,451,667, at cols. 2-4.

In some embodiments, "fumaric acid derivative" is one or more dialkyl fumarates (e.g., DMF), mono alkyl fumarates (MMF) or salts thereof.

In some of the embodiments of methods 1-5, the at least one compound being screened, evaluated, compared or used for treating a neurological disorder is not fumaric acid or its salt, or a fumaric acid derivative (e.g., DMF or MMF).

Nrf2 (Nuclear Factor-E2-related factor 2; for sequence of the Nrf2, see Accession No. AAB32188) is a transcription factor that, upon activation by oxidative stress, binds to the antioxidant response element (ARE), and activates transcription of Nrf2-regulated genes. This pathway has been well characterized for its role in hepatic detoxification and chemoprevention through the activation of phase II gene expression. ARE-regulated genes may also contribute to the maintenance of redox homeostasis by serving as endogenous anti-oxidant systems. At present, the list of Nfr2-regulated genes contains over 200 genes encoding proteins and enzymes involved in detoxification and antioxidant response (Kwak et al., J. Biol. Chem., 2003, 278:8135) such as, e.g., HO-1, ferritin, glutathione peroxidase, glutathione-S-transferases (GSTs), NAD(P)H:quinone oxidoreductases, now commonly known as nicotinamide quinone oxidoreductase 1 (NQO1; EC 1.6.99.2; also known as DT diaphorase and menadione reductase), NQO2, g-glutamylcysteine synthase (g-GCS), glucuronosyltransferase, ferritin, and heme oxygenase-1 (HO-1), as well as any one of the enzymes proteins listed in Table 1 in Chen & Kunsch, Curr. Pharm. Designs, 2004, 10:879-891; Lee et al., J. Biol. Chem., 2003, 278(14):12029-38, and Kwak, supra.

Accordingly, in some embodiments, the at least one Nrf2-regulated gene which is used to assess the activation of the Nrf2 pathway is selected from a phase II detoxification enzyme, an anti-oxidant enzyme, an enzyme of the NADPH generating system, and Nrf2 itself. Examples of the phase II detoxification enzymes include NQO1, NQO2, GST-Ya, GST-pi, GST-theta 2, GST-mu (1,2,3), microsomal GST 3, catalytic y-GCS, regulatory-GCS, microsomal epoxide hydrolase, UDP-glucuronosyltransferase, transaldolase, transketolase, and drug-metabolizing enzyme. Examples of the anti-oxidant enzymes include HO-1, ferritin (L), glutathione reductase, glutathione peroxidase, metallothionein I, thioredoxin, thioredoxin reductase, peroxiredoxin MSP23, Cu/Zn superoxide dismutase, and catalase. Examples of the enzymes of the NADPH generating system include malic enzyme, UDP-glucose dehydrogenase, malate oxidoreductase, and glucose-6-phosphate dehydrogenase.

The antioxidant response element (ARE, also referred to as the electrophile response element (EpRE), GRE1, ARE4, and StREb) is a cis-acting DNA regulatory element with a core nucleotide sequence of 5'-TGA(C/T/G)NNNGC-3' (SEQ ID NO:1) (Rushmore et al., J. Biol. Chem., 1991, 266(18):11632-9; see also Nioi et al., Mutation Res., 2004, 555:14-171).

Accordingly, in some embodiments, the DNA sequence of the ARE element, to which Nrf2 binds (whether the former is a part of an endogenous gene or an artificial construct), comprises the core ARE sequence TGA(C/T/G)NNNGC (SEQ ID NO:2) or the ARE consensus sequence (G/A)TGA(C/T/G)NNNGC(A/G) (SEQ ID NO:3). In further specific embodiments, the ARE sequence comprises any one of the "minimal enhancer" sequences shown in Table 1.

In some embodiments, the ARE sequence further comprises at least one of corresponding 5'- and 3'-USR sequences as shown in Table 1. In some embodiments, the ARE sequence comprises the sequence GTGANNNNGCA (SEQ ID NO:4), or more particularly, the mouse (NNNN=gtcg) or human (NNNN=ctca) versions thereof.

TABLE 1

| Species | Gene | Element | 5'-USR | Minimal enhancer | 3'-USR | SEQ ID NO |
|---------|------|---------|--------|------------------|--------|-----------|
| mouse | nqo1 | ARE | agTCAca | GTGAgtcgGCA | aaattt | SEQ ID NO: 5 |
| rat | NQO1 | ARE | agTCAca | GTGACttgGCA | aaatct | SEQ ID NO: 6 |
| human | NQO1 | ARE | agTCAca | GTGACtcaGCA | gaatct | SEQ ID NO: 7 |
| mouse | gsta1 | EpRE | gcTAAtg | GTGACaaaGCA | actttc | SEQ ID NO: 8 |

TABLE 1-continued

| Species | Gene | Element | 5'-USR | Minimal enhancer | 3'-USR | SEQ ID NO |
|---|---|---|---|---|---|---|
| rat | GSTA2 | ARE | gcTAAtg | GTGACaaaGCA | actttc | SEQ ID NO: 9 |
| mouse | gsta3 | ARE | ctcAggc | ATGACattGCA | tttttc | SEQ ID NO: 10 |
| rat | GSTP1 | GPE1 | agTCAct | ATGATtcaGCA | acaaaa | SEQ ID NO: 11 |
| human | GCLC | ARE4 | ccTCccc | GTGACtcaGCG | ctttgt | SEQ ID NO: 12 |
| human | GCLM | EpRE | gaagAca | ATGACtaaGCA | gaaatc | SEQ ID NO: 13 |
| mouse | ho1 | StREb | cccAAcc | ATGACacaGCA | taaaag | SEQ ID NO: 14 |
| ARE 'core' | . . . | | | TGACnnnGC | | SEQ ID NO: 15 |
| ARE consensus | . . . | | TAAnn<br>  C | ATGACnnnGCA aaaa<br>   G    T    G tttt | | SEQ ID NO: 16 |

A current model of Nrf2 function is as follows. Under basal conditions, Nrf2 is sequestered in the cytoplasm to the actin-bound Kelch-like ECH-associated protein 1 (Keap1; Accession No. NP_987096 for human Keap1), a Cullin3 ubiquitin ligase adaptor protein. More specifically, the N-terminal domain of Nrf2, known as Neh2 domain, is thought to interact with the C-terminal Kelch-like domain of Keap1. In response to xenobiotics or oxidative stress, Nrf2 is released from the Keap1/Nrf2 complex, thereby promoting nuclear translocation of Nrf2 and concomitant activation of ARE-mediated gene transcription. Keap1 function, in turn, requires association with Cullin3, a scaffold protein that positions Keap1 and its substrate in proximity to the E3 ligase Rbx1, allowing the substrate (Nrf2) to be polyubiquitinated and thus targeted for degradation. The exact mechanism of how the Keap1/Nrf2 complex senses oxidative stress is not fully understood. Human Keap1 contains 25 cysteine residues that were hypothesized to function as sensors of oxidative stress; 9 of the cysteines are thought to be highly reactive (Dinkova-Kostova et al., PNAS, 2005, 102(12):4584-9). It was theorized but is not relied on for the purposes of this invention that alkylation of cysteins leads to a conformational change, resulting in the liberation of Nrf2 from Nrf2/Keap1/Cullin3 complexes, followed by nuclear translocation of the liberated Nrf2.

In some embodiments, methods 1-3 described herein comprise contacting a cell with at least one test compound and determining whether the Nrf2 pathway is upregulated in the cell. In such methods, an upregulation of the Nrf2 pathway above a threshold (e.g., by at least 30%, 50%, 100%, 200%, 500% over a control) indicates that the at least one compound has certain biological properties beneficial in treating a neurological disease (e.g., neuroprotective properties).

The ability of a compound to activate the Nrf2 pathway can be determined by one or more in vitro and in vivo assays, including, e.g., the following assays described below.

i) Expression levels of Nrf2—The sequence of the promoter region of the nrf2 gene (−1065 to −35) has been published, for example, in Chan et al., PNAS, 1996, 93:13943-13948. One may use an artificially constructed expression construct containing the Nrf2 promoter element and an artificial reporter gene. Alternatively, one may use PCR or Northern blotting to determine expression levels of Nrf2 mRNA, or Western blotting to determine Nrf2 protein levels. Exemplary procedures for determining expression levels of Nrf2 are described in Kwak et al., Mol. Cell. Biol. 2002, 22(9):2883-2892 and Kwak et al., Mol. Med., 2001, 7:135-145. Antibodies against Nrf2 are can be produced by methods known in the art and are commercially available from, for example, Stress-Gen. Accordingly, in some embodiments, the Nrf2 pathway is activated so that the expression levels of Nrf2 are increased by, for example, at least 30%, 50%, 100%, 200%, 500% or more as compared to the non-activated state.

ii) Subcellular localization and/or nuclear translocation of Nrf2—Such assays include cell staining, or analysis of cytoplasmic versus nuclear cell extracts. For example, a Nrf2-green fluorescence protein (GFP) fusion protein construct can be made and introduced into cells and visualized as described in, e.g., Kraft et al., J. Neurosci., 2004, 24, 1101-1112; and Satoh et al., PNAS, 2006, 103(3):768-773. Accordingly, in some embodiments, the Nrf2 pathway is activated so that the ratio between cytomplasmic and nuclear Nrf2 is elevated by, for example, at least 30%, 50%, 100%, 200%, 500% or more as compared to the non-activated state.

iii) Expression levels and/or activity of one or more genes under the control of Nrf2—Such genes under the control of Nrf2 include endogenous or artificially introduced reporter genes in reporter constructs introduced into cells. For example, expression levels of endogenous or exogenously introduced NQO1 may be determined as described in the Examples. Alternatively, a reporter gene construct with one or more ARE sites operably linked to a reporter gene (e.g., luceferase or GFP) can be made, as described in, e.g., Satoh et al., PNAS, 2006, 103(3):768-773. Expression levels of an Nrf-2 induced gene product can be measured at the protein (e.g., by Western blotting or enzymatic activity assays) or at the mRNA levels (e.g., by PCR). Methods for performing RT-PCT are described in, e.g., Calabrese et al., J. Neurosci. Res., 2005, 79:509-521 for HO-1, in Wierinckx et al., J. Neuroimmunology, 2005, 166:132-143 for NQO1. Methods for measuring enzymatic activity of NQO1, using for example, menadione as a substrate, are described in Dinkova-Kostova et al., PNAS, 2001, 98:3404-09 or by Prochaska et al., Anal. Biochem., 1988, 169:328-336. Methods for measuring GST activity, using for example, 1-chloro-2,4-dinitrobenzene as a substrate, are described in Ramos-Gomez et al., J. Neurosci., 2004, 24(5):1101-1112 and Habig et al., 1974, J. Biol. Chem., 219, 7130-7139. Methods for measuring HO-1 activity are described in, e.g., in Calabrese et al., 2005, J. Neurosci. Res., 79:509-521. Accordingly, in some embodiments, the Nrf2 pathway is activated so that the expression levels and/or activity of the gene produced are increased by, for example, at least 30%, 50%, 100%, 200%, 500% or more as compared to the non-activated state.

iv) Levels of Nrf2 binding to ARE—For example, such assays may utilize electromobility shift assays (EMSA) and Chromatin Immununoprecipitation (ChIP) assay, as described in, e.g., Satoh et al., PNAS, 2006, 103(3):768-773 and Kwak et al., Mol. Cell. Biol., 2002, 22(9):2883-2892. Accordingly, in some embodiments, the Nrf2 pathway is activated so that the level of Nrf2 binding to ARE is increased by, for example, at least 30%, 50%, 100%, 200%, 500% or more as compared to the non-activated state.

v) The stability of Nrf2/Keap1 complexes—Such assay may include analysis of immunoprecipitated complexes with Nrf2 and/or Keap1 or other Nrf2/Keap1-associated proteins as described in, e.g., Satoh et al., PNAS, 2006, 103(3):768-773. Anti-Keap1 antibodies can be produced using methods known in the art and are available commercially from, for example, Santa Cruz Biotechnology. Accordingly, in some embodiments, the Nrf-2 pathway is activated so that the stability of Nrf2/Keap1 complexes is increased by, for example, at least 30%, 50%, 100%, 200%, 500% or more as compared to the non-activated state.

vi) Modification (e.g., alkylation levels) of Keap1 and other Nrf2/Keap1-associated proteins—Such assays may include mass spectrometric analysis of immunoprecipitated Keap1, using techniques as described in, e.g., Dinkova-Kostova et al., PNAS, 2005, 102(12):4584-9 and Gao et al., J. Biol. Chem., on-line pub. Manuscript M607622200. In some embodiments, the Nrf-2 pathway is activated so that the level of Keap1 and other Nrf2/Keap1-associated proteins is increased by, for example, at least 30%, 50%, 100%, 200%, 500% or more as compared to the non-activated state.

Alkylating capacity of a compound can be assessed using recombinant Keap1, by a competition reaction with 5,5'-dithiobis(2-nitrobezoic acid) (DTNB) as described in, e.g., Gao et al., J. Biol. Chem., on-line pub. Manuscript M607622200.

In some embodiments, the cell being contacted with at least one test compound is a neuron or a neuronal cell line. In some embodiments, the cell being contacted with the at least one test compound is selected from a colon carcinoma cell line (e.g., DLD1), a neuroblastoma cell line (e.g., SkNSH or IMR32), and a primary monocyte. The cell may be a cell in culture (in vitro) or be inside of an animal (in vivo).

Cell viability, and in particular, neuronal viability can be assessed in vivo or in vitro using any suitable method, including methods as described in the Examples. For example, neuronal viability can be assessed using an MTT assay after exposure of neuronal cell cultures to cytotoxic levels of glutamate as described in, e.g., Shih et al., J. Neurosci., 2005, 25(44):10321-35. Additionally, cell viability may also be assessed in assays in which cell death is induced by oxidative damage, for example, by the addition of glucose oxidase to astrocyte cell cultures, as described in, e.g., Calabrese et al., J. Neurosci. Res., 2005, 79:509-521. In vivo assays may be performed as described in, e.g., Misgeld, Histochem. Cell Biol., 2005, 124:189-196.

The amount of the reporter gene expressed can be determined by any suitable method. Expression levels, at the RNA or the protein level, can be determined using routine methods. Expression levels are usually scaled and/or normalized per total amount of RNA or protein in the sample and/or a control, which is typically a housekeeping gene such as actin or GAPDH. RNA levels are determined by quantitative PCR (e.g., RT-PCR), Northern blotting, or any other method for determining RNA levels, e.g., as described in Cloning: A Laboratory Manual, by Sambrook et al. (eds.), 2nd ed., Cold Spring Harbor Laboratory Press, 1989; Lodie et al., Tissue Eng., 2002, 8(5):739-751); or as described in the Examples. Protein levels are determined using, Western blotting, ELISA, enzymatic activity assays, or any other method for determining protein levels as described in, e.g., Current Protocols in Molecular Biology, by Ausubel et al. (eds.), John Wiley and Sons, 1998.

Expression levels may also be determined using reporter gene assays in cell/tissue extracts or by tissue or whole-animal imaging. In addition to MRI, tissue imaging on living animals can be performed by fluorescence detection (Hoffman Lancet Oncol., 2002 3:546-556; Tung et al., Cancer Res., 2000, 60:4953-4958), bioluminescence detection (Shi et al., PNAS, 2001, 98:12754-12759; Luke et al., J. Virol., 2002, 76:12149-12161; and U.S. Pat. Nos. 5,650,135 and 6,217,847), positron emission tomography (Liang et al., Mol. Ther., 2002, 6:73-82, near-infrared fluorescence (Tung et al., Cancer Res., 2000, 60:4953-4958), or X-ray imaging (Hemminki et al., J. Nat. Cancer Inst., 2002, 94:741-749).

A neurological disease in methods 1-5 above can be a neurodegenerative disease such as, for example, ALS, Parkinson's disease, Alzheimer's disease, and Huntington's disease. The neurological disease can also be multiple sclerosis (MS), or other demyelinating diseases of the central or peripheral nervous system. In some embodiments the form of MS in methods 1-5 is selected from: relapsing remitting MS (RRMS), secondary progressive MS (SPMS), primary progressive MS (PPMS), and malignant MS (Marburg Variant).

The subject being treated or administered the compound as per methods described herein, is a mammal in need thereof, such as a subject in need of neuroprotection, including a subject who has or is at risk for developing a demyelinating and another specified neurodegenerative disease. The subject is mammalian, and can be a rodent or another laboratory animal, e.g., a non-human primate. In some embodiments, the subject is human.

Neurodegenerative diseases are described in, for example, Neurodegenerative Diseases: Neurobiology, Pathogenesis and Therapeutics, M. Flint Beal, Anthony E. Lang, Albert C. Ludolph, Cambridge University Press (Jul. 11, 2005). Examples of neurological diseases suitable for the methods described herein include neurodegenerative diseases such as amyotrophic lateral sclerosis (ALS), Parkinson's disease, Alzheimer's disease, and Huntington's disease. Other examples include demyelinating neurological disease including, in addition to MS, the following diseases: acute haemorrhagic leucoencephalomyelitis, Hurst's disease, acute disseminated encephalomyelitis, optic neuritis, Devic's disease, spinal cord lesions, acute necrotizing myelitis, transverse myelitis, chronic progressive myelopathy, progressive multifocal leukoencephalopathy (PML), radiation myelopathy, HTLV-1 associated myelopathy, monophasic isolated demyelination, central pontine myelinolysis, and leucodystrophy (e.g., adrenoleucodystrophy, metachromatic leucodystrophy, Krabbe's disease, Canavan's disease, Alexander's disease, Pelizaeus-Merbacher disease, vanishing white matter disease, oculodentodigital syndrome, Zellweger's syndrome), chronic inflammatory demyelinating polyneuropathy (CIDP), acute inflammatory demyelinating polyneuropathy (AIDP), Leber's optic atrophy, and Charcot-Marie-Tooth disease.

Additional examples of diseases suitable for the methods described herein include polyneuritis and mitochondrial disorders with demyelination. These disorders may be co-presented with, and possibly aggravated by diabetes, e.g., insulin-dependent diabetes mellitus (IDDM; type I diabetes), or other diseases.

A test compound may be further assayed in an animal model of MS, known as Experimental Autoimmune Encephalomyelitis (EAE) (Tuohy et al., J. Immunol., 1988, 141:1126-1130, Sobel et al. J. Immunol., 1984, 132:2393-2401, and Traugott, Cell Immunol., 1989 119:114-129). Chronic relapsing EAE provides a well established experimental model for testing agents that would be useful for the treatment of MS. The mouse EAE is an induced autoimmune demyelinating disease with many similarities to human MS in its clinical manifestations. In both EAE and MS, clinical disease is associated with blood-brain barrier (BBB) dysfunction, infiltration of central nervous system by mononuclear cells (mainly macrophages and T lymphocytes, and serum products), and demyelination (Baker et al. J. Neuroimmunol., 1990, 28:261; Butter et al., J. Neurol. Sci., 1991, 104:9; Harris et al., Ann. Neurol., 1991, 29:548; Kermonde et al., Brain, 1990, 113:1477).

Clinical signs of MS and demyelinating pathology in EAE result from immunization with CNS myelin proteins or peptides (e.g., MBP, PLP, and MOG) under Th1 conditions (direct immunization model), or by adoptive transfer of CNS antigen-specific Th1 cells (adoptive transfer model) (Ben-Nun et al., Eur. J. Immunol., 1981, 11:195-199; Ando et al., Cell Immunol., 1989, 124:132-143; Zamvil et al., Nature, 1985, 317:355-358; Zamvil et al., Ann. Rev. Immunol., 1990, 8:579-621). For example, in the SJL mouse model of EAE, immunization with the CNS peptide PLP 139-151 or adoptive transfer of PLP-specific Th1 cells results in a disease course consisting of an acute phase with loss of tail tone on day 10 to day 12, followed by hind limb paralysis and CNS mononuclear cell infiltration (Tuohy et al., J. Immunol., 1988, 141:1126-1130, Sobel et al., J. Immunol., 1984, 132:2393-2401, and Traugott, Cell Immunol., 1989, 119:114-129). Resolution of clinical signs and recovery occurs on day 20 to day 25 and the animals may undergo several more relapses less severe than the initial phase. EAE has been used to evaluate new therapeutic approaches to T-cell-mediated autoimmune disease because of the clinical and histopathological similarities to the human demyelinating MS.

The ability of a compound to slow or prevent neurodegeneration (including demyelination and neuronal death) can be assessed in the EAE model or another animal model, including for example, Thieler's murine encephalomyelitis virus (TMEV)-induced demyelinating disease, murine hepatitis virus (MHV), Semliki Forest Virus, or Sindbis virus as described in, e.g., Ercoli et al., J. immunol., 2006, 175:3293-3298.

A compound may be optionally tested in at least one additional animal model (see, generally, Immunologic Defects in Laboratory Animals, eds. Gershwin et al., Plenum Press, 1981), for example, such as the following: the SWR×NZB (SNF1) mouse model (Uner et al., J. Autoimmune Disease, 1998, 11(3):233-240), the KRN transgenic mouse (K/B×N) model (Ji et al., Immunol. Rev., 1999, 69:139); NZB×NZW (B/W) mice, a model for SLE (Riemekasten et al., Arthritis Rheum., 2001, 44(10):2435-2445); the NOD mouse model of diabetes (Baxter et al., Autoimmunity, 1991, 9(1):61-67), etc.); or mouse models of multiple sclerosis (see, e.g., Linker et al., Eur. J. Immunol., 2002, 8(6):620-624, and Eugster et al., Nat. Med., 1999, 29:626-632; and Gold et al., Brain, 2006, 129:1953-1971).

Preliminary doses, for example, as determined in animal tests, and the scaling of dosages for human administration is performed according to art-accepted practices. Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In some embodiments compositions that exhibit large therapeutic indices are used.

The therapeutically effective dose can be estimated initially from cell culture assays. A dose may be formulated in animal models to achieve a circulating plasma concentration range that includes the $IC_{50}$ (i.e., the concentration of the therapeutic compound which achieves a half-maximal inhibition of symptoms) as determined in cell culture assays or animal models. Levels in plasma may be measured, for example, by ELISA or HPLC. The effects of any particular dosage can be monitored by a suitable bioassay. Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

The data obtained from the in vitro assays or animal studies can be used in formulating a range of dosages for use in humans. Therapeutically effective dosages achieved in one animal model can be converted for use in another animal, including humans, using conversion factors known in the art (see, e.g., Freireich et al., Cancer Chemother. Reports, 1966, 50(4):219-244 and Table 2 for Equivalent Surface Area Dosage Factors).

TABLE 2

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

In some embodiments the dosage of such compounds lies within a range of circulating concentrations that include the $ED_{50}$ with little or no toxicity. In some embodiments the dosage varies within this range depending upon the dosage form employed and the route of administration utilized. Generally, a therapeutically effective amount may vary with the subject's age, condition, and sex, as well as the severity of the medical condition in the subject. Examples of pharmaceutically acceptable dosages for compounds described herein are from 1 µg/kg to 25 mg/kg, depending on the compounds, severity of the symptoms and the progression of the disease. The appropriate therapeutically effective doses can be selected by a treating clinician and in some embodiments range approximately from 1 µg/kg to 20 mg/kg, from 1 µg/kg to 10 mg/kg, from 1 µg/kg to 1 mg/kg, from 10 µg/kg to 1 mg/kg, from 10 µg/kg to 100 µg/kg, from 100 µg to 1 mg/kg. Additionally, certain specific dosages are indicated in the Examples.

For DMF or MMF, an effective amount can range from 1 mg/kg to 50 mg/kg (e.g., from 2.5 mg/kg to 20 mg/kg or from 2.5 mg/kg to 15 mg/kg). Effective doses will also vary, as recognized by those skilled in the art, dependent on route of administration, excipient usage, and the possibility of co-usage with other therapeutic treatments including use of other therapeutic agents. For example, an effective dose of DMF or MMR to be administered to a subject orally can be from about 0.1 g to 1 g per pay, 200 mg to about 800 mg per day (e.g., from about 240 mg to about 720 mg per day; or from about 480 mg to about 720 mg per day; or about 720 mg per day). For example, the 720 mg per day may be administered in separate administrations of 2, 3, 4, or 6 equal doses.

The dosage may be determined by a physician and adjusted, as necessary, to suit observed effects of the treatment. The compositions may be given as a bolus dose, to maximize the circulating levels for the greatest length of time after the dose. Continuous infusion may also be used after the bolus dose.

In some embodiments, compositions used in the methods described herein further comprise a pharmaceutically acceptable excipient. As used herein, the phrase "pharmaceutically acceptable excipient" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition is formulated to be compatible with its intended route of administration. Methods to accomplish the administration are known in the art. "Administration" is not limited to any particular delivery system and may include, without limitation, parenteral (including subcutaneous, intravenous, intramedullary, intraarticular, intramuscular, or intraperitoneal injection), rectal, topical, transdermal, or oral (for example, in capsules (e.g., as, poweder, granules, microtablet, micropellets, etc.), suspensions, or tablets). Examples of some of formulations containing DMF and/or MMF are given in, e.g., U.S. Pat. Nos. 6,509,376, and 6,436,992.

Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable salt forms and standard pharmaceutical formulation techniques and excipients are well known to persons skilled in the art.

The following Examples are intended for illustrative purposes and do not limit the inventions claimed.

EXAMPLES

Example 1

Human colon carcinoma DLD1 cells were treated with DMF or MMF at indicated concentrations (5, 15, or 50 µM) for 16 hours, rinsed with PBS, and harvested into reducing SDS sample buffer. The lysates were subjected to SDS PAGE and the separated proteins were electrophoretically transferred onto nitrocellulose membranes for Western blot analysis. To detect Nrf2 and NQO1, the membranes were incubated with the respective primary antibodies overnight at 4° C., washed, and incubated with peroxidase-conjugated secondary antibodies followed by the chemiluminescent peroxidase substrate. Detection of the target protein band luminescence and image acquisition were done using CCD-equipped imaging station Kodak2000R. The results shown in FIG. 1, demonstrate that DMF and MMF are potent activators of Nrf2 at concentrations within clinical exposure range.

Example 2

DLD1 cells were grown in MEM supplemented with 10% fetal bovine serum. The cells were transfected with the indicated siRNA's using the Lipofectamine reagent (Invitrogen) according to the manufacturer's instructions and 30 hrs later stimulated with 30 µM DMF for 40 hours. The cells were harvested and processed for Western blotting analysis of Nrf2 and NQO1 levels as described in Example 1. Sources and the identity of reagents used in Examples 1 and 2 are specified Table 3 below:

|  | Target | Reagent | Source/Sequence | Vendor |
| --- | --- | --- | --- | --- |
| Primary Antibody | Nrf2 | Nrf2 (T-19) | goat polyclonal antibody | Santa Cruz Biotechnology |
|  | Keap1 | Keap1 (E-20) | goat polyclonal antibody | Santa Cruz Biotechnology |
|  | NQO1 | NQO1 (A180) | mouse monoclonal antibody | Santa Cruz Biotechnology |
|  | GAPDH | Anti-GAPDH | mouse monoclonal antibody | Ambion |
| Secondary antibody | anti-mouse | HRP-Mouse IgG | sheep | Amersham Biosciences |
|  | anti-rabbit | HRP-Rabbit IgG | donkey | Amersham Biosciences |
|  | anti-goat | HRP-Goat IgG | Bovine | Santa Cruz Biotechnology |
| siRNA | Nrf2 | Nrf2-2 | UCAUUGAACUGCUCUUUGGUU (antisense) (SEQ ID NO: 17) | Dharmacon |
|  | Keap1 | Keap1-1 | GAAUUAAGGCGGUUUGUCCUU (antisense) (SEQ ID NO: 18) | Dharmacon |

Figure 2:
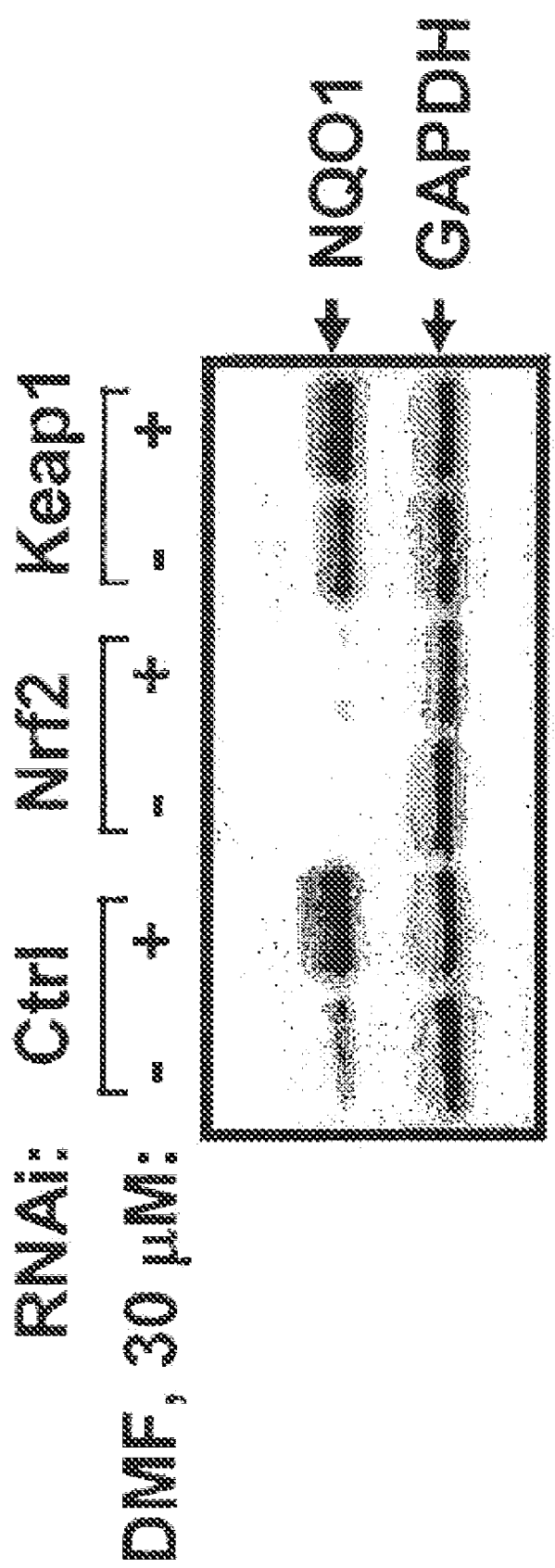
FIG. 2 shows results of RNAi experiments.

The results are shown in FIG. 2 (for ease of representation, the image of the Western blot is turned upside down). The results demonstrate that DMF-induced upregulation of NQO1 requires Nrf2 and can be mimicked by activation of Nrf2 through repression of Keap1. Therefore, DMF acts as an Nrf2 agonist causing cellular accumulation of Nrf2 and Nrf2 target gene expression.

Example 3

For induction of EAE, mice received s.c. injections in the flanks and tail base of 50 µg MOG 35-55 peptide in PBS emulsified in an equal volume of complete Freund's adjuvant (CFA) containing *Mycobacterium tuberculosis* H37RA (Difco, Detroit Mich., USA) at a final concentration of 0.5 mg/ml. Two injections of pertussis toxin (List Biological Laboratories Inc., California, USA; 200 μg per mouse i.p) were given on days 0 and 2.

DMF and MMF was diluted in 200 μl 0.08% Methocel/ $H_2O$ as vehicle and administered by oral gavage starting from day 3 post immunization (p.i) until termination. Each treatment group consisted of 8 animals: vehicle alone as a negative control, 5 mg/kg body weight DMF twice a day, 15 mg/kg body weight DMF twice a day, 15 mg/kg body weight MMF twice a day. The compounds were obtained via Fumapharm AG. Oral gavage was used to ensure exact dosing and to avoid compound degradation.

Spinal cord tissues were fixed in 4% paraformaldehyde and embedded in paraffin. Slides were deparaffinized and rehydrated in graded alcohol solutions. Antigen retreival was performed by immersing the slides in 10 mM Citrate, pH 6.0 for 20 minutes in a pressure cooker at 120 C (Pascal, Dako Cytomation).

Immunohistochemistry was performed using the Dako autostainer as follows. Endogenous peroxidase was quenched by a 10 minute incubation in 3% $H_2O_2$/Methanol. The rabbit anti Nrf2 antibody C-20 (sc-722, Santa Cruz Biotechnology) was added at a 1:250 dilution in Dako Diluent with Background Reducing Components (Dako # S3022) C-20 antibody was detected using the Envision anti rabbit labeled polymer-HRP (Dako #K4003) and DAB (Vector Labs #SK-4100) was used as the chromogenic substrate. Morphometric analysis of Nrf2 immunostaining was performed using ImageJ software from NIH.

Figure 3:
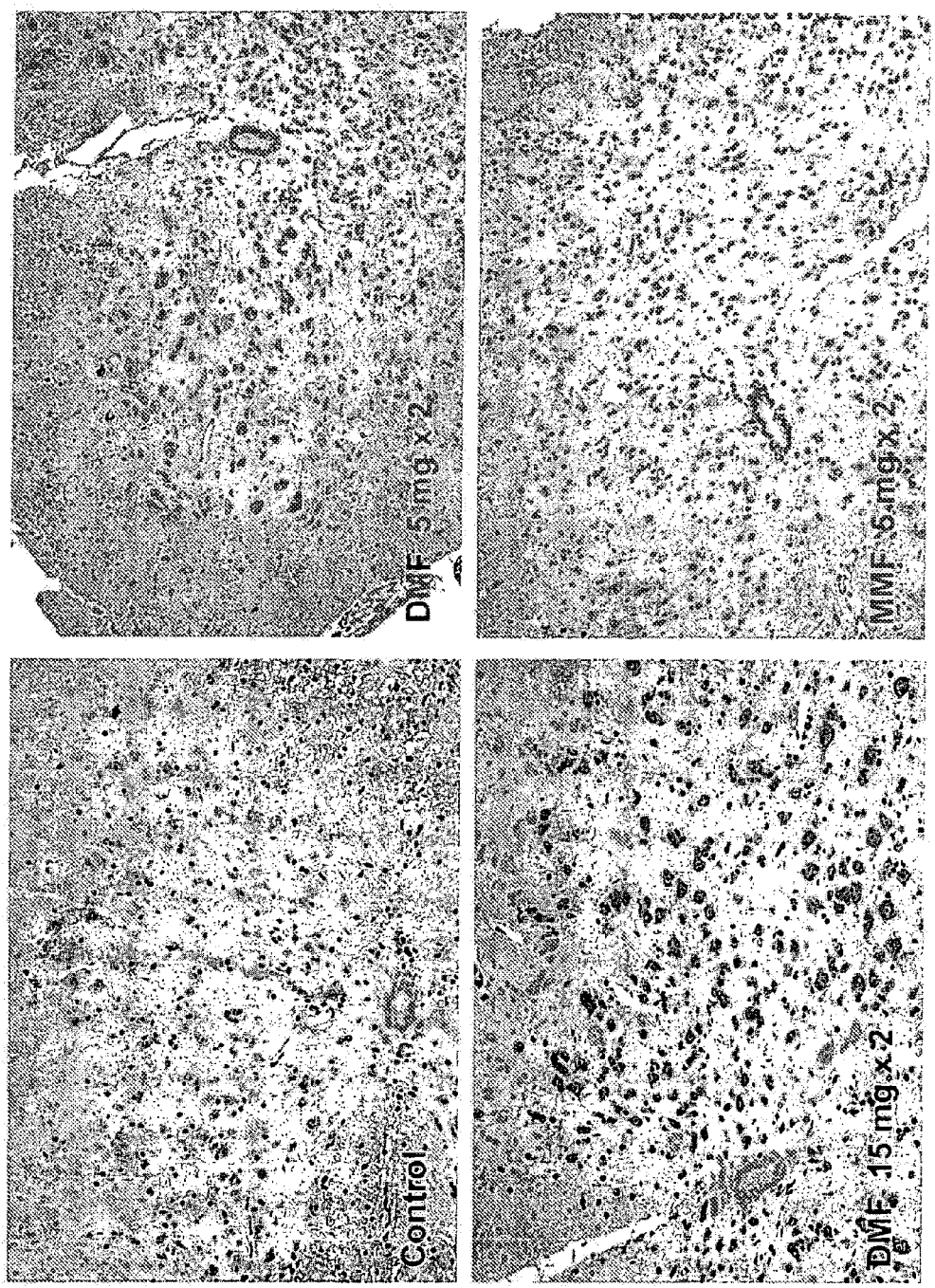
FIG. 3 shows evidence of Nrf2 activation by DMF and MMF In vivo.
Figure 4:
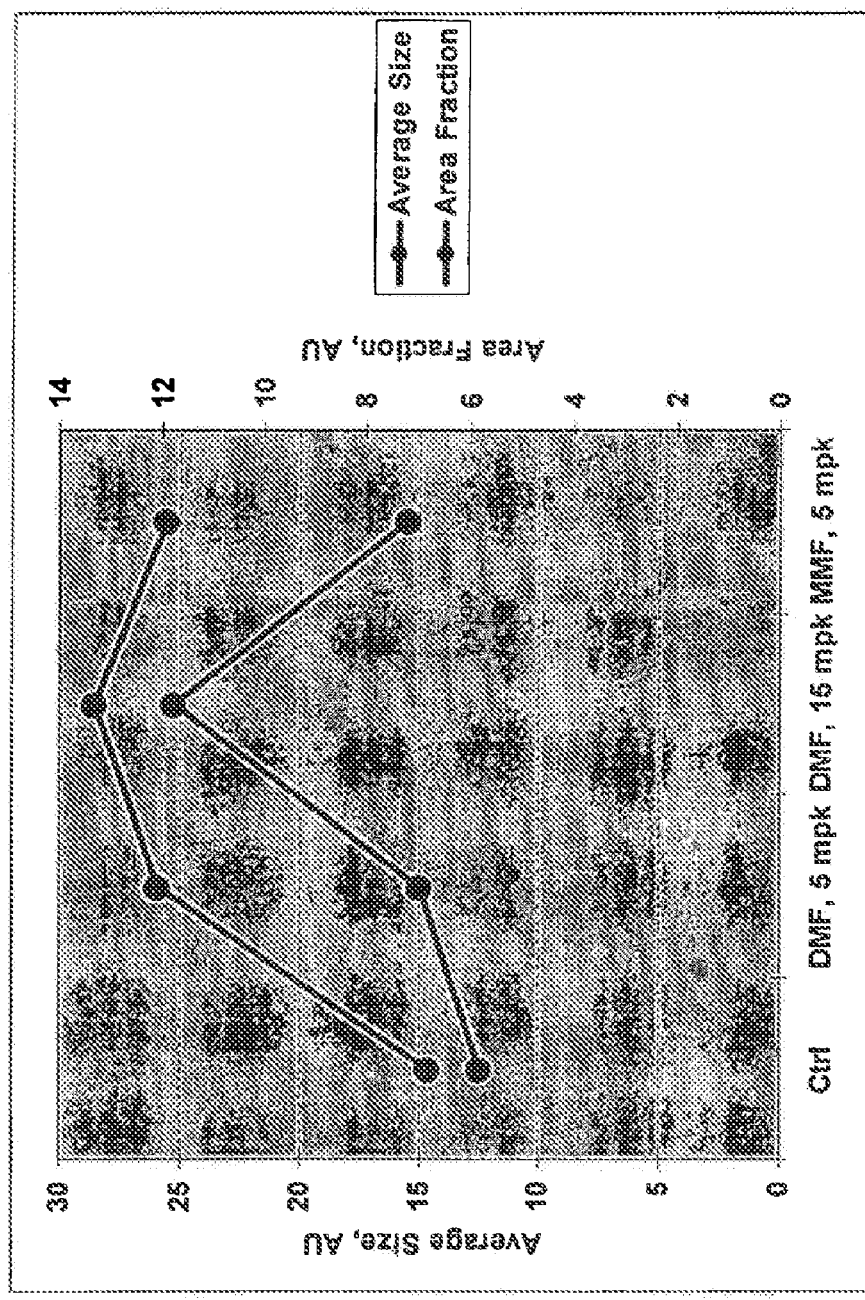
FIG. 4 shows evidence of Nrf2 activation by DMF and MMF In vivo.

The results, shown in FIGS. 3 and 4, demonstrate MMF and DMF activation of Nrf2 in vivo.

All publications and patent documents cited herein are incorporated by reference in their entirety. To the extent the material incorporated by reference contradicts or is inconsistent with the present specification, the present specification will supersede any such material.

---

The invention claimed is:

1. A method of treating a subject in need of treatment for multiple sclerosis comprising orally administering to the subject in need thereof a pharmaceutical composition consisting essentially of (a) a therapeutically effective amount of dimethyl fumarate, monomethyl fumarate, or a combination thereof, and (b) one or more pharmaceutically acceptable excipients, wherein the therapeutically effective amount of dimethyl fumarate, monomethyl fumarate, or a combination thereof is about 480 mg per day.

2. The method of claim 1, wherein the pharmaceutical composition is administered in the form of a tablet, a suspension, or a capsule.

3. The method of claim 1, wherein the therapeutically effective amount is administered in separate administrations of 2, 3, 4, or 6 equal doses.

4. The method of claim 3, wherein the therapeutically effective amount is administered in separate administrations of 2 equal doses.

5. The method of claim 3, wherein the therapeutically effective amount is administered in separate administrations of 3 equal doses.

6. The method of claim 1, wherein the pharmaceutical composition consists essentially of dimethyl fumarate and one or more pharmaceutically acceptable excipients.

7. The method of claim 1, wherein the pharmaceutical composition consists essentially of monomethyl fumarate and one or more pharmaceutically acceptable excipients.

8. The method of claim 1, wherein the pharmaceutical composition is administered to the subject for at least 12 weeks.

9. The method of claim 6, wherein the therapeutically effective amount is administered to the subject in 2 equal doses.

10. The method of claim 9, wherein the therapeutically effective amount is administered to the subject for at least 12 weeks.

11. A method of treating a subject in need of treatment for multiple sclerosis consisting essentially of orally administering to the subject about 480 mg per day of dimethyl fumarate, monomethyl fumarate, or a combination thereof.

12. The method of claim 11, wherein about 480 mg of dimethyl fumarate per day is administered to the subject.

13. The method of claim 12, wherein the dimethyl fumarate is administered in separate administrations of 2 equal doses.

14. The method of claim 12, wherein the dimethyl fumarate is administered in separate administrations of 3 equal doses.

15. A method of treating a subject in need of treatment for multiple sclerosis comprising orally administering to the subject pharmaceutical composition consisting essentially of (a) a therapeutically effective amount of dimethyl fumarate and (b) one or more pharmaceutically acceptable excipients, wherein the therapeutically effective amount of dimethyl fumarate is about 480 mg per day.

16. The method of claim 15, wherein the dimethyl fumarate is administered in separate administrations of 2 equal doses.

17. The method of claim 1, wherein the expression level of NQO1 in the subject is elevated after administering to the subject the therapeutically effective amount of dimethyl fumarate, monomethyl fumarate, or a combination thereof.

18. The method of claim 11, wherein the expression level of NQO1 in the subject is elevated after administering to the subject about 480 mg per day of dimethyl fumarate, monomethyl fumarate, or a combination thereof.

19. The method of claim 15, wherein the expression level of NQO1 in the subject is elevated after administering to the subject the therapeutically effective amount of dimethyl fumarate.

20. A method of treating a subject in need of treatment for multiple sclerosis comprising treating the subject in need thereof with a therapeutically effective amount of dimethyl fumarate, monomethyl fumarate, or a combination thereof, wherein the therapeutically effective amount of dimethyl fumarate, monomethyl fumarate, or a combination thereof is about 480 mg per day.

* * * * *